(12) United States Patent
Miyakoshi et al.

(10) Patent No.: US 8,266,943 B2
(45) Date of Patent: Sep. 18, 2012

(54) FLOW RATE ESTIMATION DEVICE FOR A BLOOD PUMP AND A BLOOD PUMP SYSTEM INCLUDING THE DEVICE

(75) Inventors: Takayuki Miyakoshi, Nagano (JP); Kenji Yamazaki, Tokyo (JP)

(73) Assignee: Sun Medical Technology Research Corporation, Nagano (JP)

( * ) Notice: Subject to any disclaimer, the term of this patent is extended or adjusted under 35 U.S.C. 154(b) by 0 days.

(21) Appl. No.: 12/963,302

(22) Filed: Dec. 8, 2010

(65) Prior Publication Data
US 2011/0077782 A1 Mar. 31, 2011

Related U.S. Application Data

(63) Continuation of application No. 12/357,164, filed on Jan. 21, 2009, now Pat. No. 7,861,582, which is a continuation of application No. 11/553,347, filed on Oct. 26, 2006, now Pat. No. 7,497,116.

(51) Int. Cl.
*A61M 1/10* (2006.01)
(52) U.S. Cl. .......... 73/1.16; 73/168; 73/861.08; 417/20; 417/22
(58) Field of Classification Search .................. 73/1.16, 73/168, 861.01, 861.04, 861.06, 861.08; 417/20, 22, 43, 300; 600/16, 17
See application file for complete search history.

(56) References Cited

U.S. PATENT DOCUMENTS

| 4,589,822 | A | 5/1986 | Clausen et al. |
| 4,606,698 | A | 8/1986 | Clausen et al. |
| 4,781,525 | A | 11/1988 | Hubbard et al. |
| 6,066,086 | A | 5/2000 | Antaki et al. |
| 6,135,943 | A | 10/2000 | Yu et al. |
| 6,142,752 | A | 11/2000 | Akamatsu et al. |
| 6,610,004 | B2 | 8/2003 | Viole et al. |
| 6,747,064 | B2 | 6/2004 | Emanuele et al. |
| 6,808,508 | B1 | 10/2004 | Zafirelis et al. |
| 6,878,272 | B2 | 4/2005 | Kawaguchi |
| 7,033,147 | B2 | 4/2006 | Yanai et al. |
| 2002/0094281 | A1 | 7/2002 | Khanwilkar et al. |
| 2003/0223879 | A1 | 12/2003 | Yanai et al. |
| 2004/0064012 | A1 | 4/2004 | Yanai |
| 2005/0004418 | A1 | 1/2005 | Morello |
| 2005/0014991 | A1 | 1/2005 | Sugiura |
| 2005/0196293 | A1 | 9/2005 | Ayre et al. |
| 2005/0267322 | A1 | 12/2005 | LaRose |
| 2007/0232934 | A1 | 10/2007 | LaRose et al. |

FOREIGN PATENT DOCUMENTS

| JP | 2003210572 A | 7/2003 |
| JP | 2005048660 A | 2/2005 |
| JP | 2005296528 A | 10/2005 |

*Primary Examiner* — David Rogers
(74) *Attorney, Agent, or Firm* — Lowe Hauptman Ham & Berner LLP

(57) ABSTRACT

In a flow rate estimation device of a blood pump, a general flow rate estimation formula which includes a correction term is formed based on a plurality of blood pumps. Measured data obtained from an objective blood pump implanted inside a patient is substituted into the correction term, thus forming a flow rate estimation formula of the objective blood pump. The flow rate Q of the objective blood pump is estimated based on the flow rate estimation formula and the values of the rotational speed N and the consumption current I of the motor of the objective blood pump, and the attribute data Z of the blood of the patient.

12 Claims, 14 Drawing Sheets

FLOW RATE ESTIMATION DEVICE FOR A BLOOD PUMP AND A BLOOD PUMP SYSTEM INCLUDING THE DEVICE

RELATED APPLICATIONS

The present application is a Continuation of U.S. application Ser. No. 12/357,164, filed Jan. 21, 2009, which is a continuation of U.S. application Ser. No. 11/553,347, filed Oct. 26, 2006, which claims priority from Japanese Application Number 2004-120941filed Apr. 15, 2004, the disclosures of all of the above listed applications are hereby incorporated by reference herein in their entirety.

TECHNICAL FIELD

The present invention relates to a flow rate estimation method of a blood pump, a flow rate estimation device of a blood pump, a blood pump system, and a storage medium.

BACKGROUND OF THE INVENTION

As one of medical treatments for curing a Serious heart disease patient, treatment which uses an implantable blood pump has been performed. To appropriately perform the treatment, it is necessary to accurately find a flow rate of the blood pump. Accordingly, a blood flow meter such as a blood flow meter based on a thermodilution method, a blood flow meter based on a dye dilution method, an electromagnetic blood flow meter, an ultrasonic blood flow meter, a blood flow meter based on a transesophageal echocardiography, a blood flow meter based on a transthoracic echocardiography or a blood flow meter based on an electric impedance method is mounted inside or outside a body of a patient, and the flow rate of the implantable blood pump is measured.

However, with respect to the blood flow meter such as the blood flow meter based on the thermodilution method, the blood flow meter based on the dye dilution method, the electromagnetic blood flow meter or the ultrasonic blood flow meter, it is necessary to mount such a blood flow meter inside the body of the patient, and hence, the use of the blood flow meter is considerably invasive to the patient. Accordingly, the mounting of the blood flow meter inside the body of the patient is limited for a certain period postoperatively in an actual use, and hence, after removing the blood flow meter from the body of the patient, a method which allows a user to know the flow rate of the blood pump without using the blood flow meter becomes necessary.

In addition, with respect to the blood flow meter such as the blood flow meter based on the transesophageal echocardiography, the blood flow meter based on the transthoracic echocardiography or the blood flow meter based on the electric impedance method, steps for measuring the flow rate of blood are cumbersome in an actual operation, and hence, it is also fairly invasive to the patient. Accordingly, a method which allows a user to know the flow rate of the blood pump without using the blood flow meter also becomes necessary.

FIG. 14 and FIG. 15 are views for explaining a conventional blood pump system which satisfies such demands as mentioned above.

The conventional blood pump system 901 includes, as shown in FIG. 14 and FIG. 15, a blood pump 905 which discharges blood by rotating an impeller 921 by making use of a rotational force of a motor 934 as a driving power source, a viscosity/rotational-speed/motor-current/discharge-flow-rate related data storing part 960 which stores "predetermined viscosity-related discharge-flow-rate data" which is constituted of various motor current/discharge flow rate related data at various different impeller rotational speeds under a predetermined liquid viscosity with respect to various different predetermined viscosities, a blood parameter input part 957, a sensor circuit 955 which has a function of measuring and calculating an impeller rotational speed which measures the rotational speed of the impeller 921, a motor current measuring part which has a function of measuring a current supplied to the motor 934, and a discharge flow rate arithmetic calculation part 958 which calculates a liquid discharge flow rate based on liquid viscosity, a motor current and an impeller rotational speed using the liquid viscosity, the impeller rotational speed, the motor current, and viscosity/rotational speed/motor current/discharge flow rate related data (for predetermined viscosity-related discharge-flow-rate data table, see FIG. 15).

According to the blood pump system 901, as shown in FIG. 14 and FIG. 15, since the impeller rotational speed, the motor current and the blood viscosity are measured and, thereafter, a blood discharge flow rate is calculated based on the measured values and the predetermined viscosity-related discharge-flow-rate data table, the flow rate of the blood pump can be estimated without using any blood flow meter.

Further, according to the blood pump system 901, as shown in FIG. 14 and FIG. 15, since the blood discharge flow rate is calculated based on the predetermined viscosity-related discharge-flow-rate data table, that is, the minimal number of individual data which satisfies the required accuracy is stored as a data table and the blood discharge flow rate is calculated selectively using the data close to a current value to be calculated or the like, the accurate flow rate can be easily obtained in comparison with a case that the blood discharge flow rate is calculated based on a relationship formula of the impeller rotational speed, the motor current, the blood viscosity, and the flow rate of the blood pump (see patent document 1, for example).

[Patent document 1]
JP-A-2003-210572

DISCLOSURE OF THE INVENTION

Problems to be Solved by the Invention

However, in case of implantable blood pumps, it is not easy to eliminate the individual difference of a blood pump property because of limitations on the structure. Accordingly, when the flow rate of the blood pump is estimated using the above-mentioned method according to the conventional blood pump system 901, the estimation accuracy of the flow rate of each blood pump is lowered due to the individual difference of the blood pump property, and hence, there arises a drawback that the medical treatment which uses the implantable blood pump cannot be properly performed.

Accordingly, the present invention has been made to overcome such a drawback, and it is an object of the present invention to provide a flow rate estimation method of a blood pump and a flow rate estimation device of a blood pump, which can effectively suppress the lowering of accuracy of a flow rate estimation result attributed to the individual difference of the blood pump property. It is another object of the present invention to provide a blood pump system which includes such a flow rate estimation device of a blood pump. It is still another object of the present invention to provide a storage medium which is necessary for realizing such a flow rate estimation device of a blood pump.

Means for Solving the Problems (1) A flow rate estimation method of a blood pump according to the present invention is a method which estimates a flow rate Q of the blood pump which discharges blood using a rotational force of a motor as a driving power source based on a rotational speed N of the motor, a consumption current I of the motor and an attribute data Z of blood of a patient, and is characterized in that the flow rate estimation method of a blood pump includes a first step which forms flow rate estimation information which describes the relationship among the rotational speed of the motor, the consumption current of the motor and the flow rate of an objective blood pump or a blood pump for flow rate estimation, and the attribute data of a liquid, and a second step which estimates the flow rate Q of the blood pump based on the flow rate estimation information and the values of N, I and Z which are obtained by measuring the rotational speed N of the motor and the consumption current I of the motor in the objective blood pump which is implanted inside the body of the patient and the attribute data Z of the blood of the patient.

According to the flow rate estimation method of a blood pump of the present invention, the flow rate estimation information is formed for every objective blood pump on which the flow rate estimation is performed in the first step, and the flow rate estimation is performed on the objective blood pump based on the flow rate estimation information in the second step, and hence, there is no deterioration of accuracy of the flow rate estimation result attributed to the individual difference of the characteristic of the blood pump, thus achieving the object of the present invention.

In the flow rate estimation method of a blood pump of the present invention, "objective blood pump" implies a blood pump on which the flow rate estimation is performed.

Further, "a plurality of blood pumps" described later implies a plurality of arbitrary blood pumps on which the property (such as general flow rate estimation information or the like explained later) of the blood pumps are measured and evaluated out of the blood pumps having the same standard and specification as the "objective blood pump".

Further, in the flow rate estimation method of a blood pump of the present invention, "liquid" indicates liquid which flows in the blood pump at forming the flow rate estimation information and may be either "test liquid" or "blood of patient".

(2) In the flow rate estimation method of a blood pump as mentioned in the above (1), the flow rate estimation information may be a flow rate estimation formula.

By adopting such a method, by substituting the value of the rotational speed N of the motor, the consumption current I of the motor and the attribute data Z of the blood of the patient which are measured in the second step in the flow rate estimation formula, it becomes possible to easily perform the flow rate estimation of the blood pump.

(3) In the flow rate estimation method of a blood pump as mentioned in the above (1), the flow rate estimation information may be a flow rate estimation table.

By adopting such a method, it is possible to easily perform the flow rate estimation of the blood pump by selectively referring to portions of the flow rate estimation table which approximate the rotational speed N of the motor, the consumption current I of the motor and the attribute data Z of the blood of the patient which are measured in the second step and, at the same time, performing a proper complementary calculation.

(4) In the flow rate estimation method of a blood pump as mentioned in the above (1), the first step may be a step which forms the flow rate estimation information by measuring the actual flow rate of the objective blood pump using a blood flow meter when the rotational speed of the motor and the consumption current of the motor in the objective blood pump and the attribute data of the test liquid are respectively changed.

The step for forming the flow rate estimation information is cumbersome in general, and hence requires considerable time and procedure. This is because that the formation of the flow rate estimation information requires the measurement of the flow rate of the blood pump by respectively changing the rotational speed of the motor, the consumption current of the motor and the attribute data of the liquid.

However, according to the flow rate estimation method of the blood pump described in the above (4), the flow rate estimation information is formed using the test liquid, and hence, it is possible to finish such a cumbersome and time-consuming first step before shipping in advance.

Further, it is possible to perform such a cumbersome and time-consuming first step before implanting the objective blood pump into a body of a patient, and hence, there is no possibility that a burden imposed on the patient is increased.

Still further, by performing the formation of the flow rate estimation information for every objective blood pump beforehand, immediately after implanting the objective blood pump inside the body of the patient, it is possible to accurately perform the flow rate estimation with respect to the objective blood pump.

(5) In the flow rate estimation method of a blood pump as mentioned in the above (1), the first step may include a step which forms general flow rate estimation information including correction information by measuring flow rates of blood pumps using a blood flow meter when the rotational speeds of the motors and the consumption currents of the motors in a plurality of respective blood pumps, and the attribute data of a test liquid are respectively changed, and a step in which the rotational speed of the motor and the consumption current of the motor in the objective blood pump, and the attribute data of the test liquid are measured, and the flow rate of the blood pump is measured using the flow meter, and the flow rate estimation information on the objective blood pump is formed based on the general flow rate estimation information by substituting the obtained measured data into the correction information.

By adopting such a method, in the same manner as the case of the flow rate estimation method of a blood pump described in the above (4), the flow rate estimation information is formed using the test liquid, and hence, it becomes possible to finish such a cumbersome and time-consuming first step before shipping in advance.

Further, since such a cumbersome and time-consuming first step can be performed before implanting the objective blood pump inside the body of the patient, there is no possibility that a burden imposed on a patient is increased.

Still further, by performing the formation of the flow rate estimation information for every objective blood pump beforehand, immediately after implanting the objective blood pump inside the body of the patient, it becomes possible to accurately perform the flow rate estimation with respect to the objective blood pump.

Further, in the flow rate estimation method of the blood pump described in the above (5), the formation of the flow rate estimation information which is originally cumbersome and time-consuming is divided into the former step which forms the general flow rate estimation information including the correction information and the latter step which forms the flow rate estimation information on the objective blood pump based on the general flow rate estimation information by substituting the measured data obtained for every objective blood pump into the correction information, wherein among these steps, the former step which is originally cumbersome and time-consuming is performed preliminarily using a plurality of blood pumps, and the latter step which is relatively less time-consuming (unnecessary to perform measurement by respectively changing the rotational speed of the motor, the consumption current of the motor and the attribute data of the test liquid different from the former step) is performed using the objective blood pump, whereby it becomes possible to further easily form the flow rate estimation information as a whole compared to the flow rate estimation method of the blood pump described in the above (4).

Here, while the general flow rate estimation information including the correction information is the information necessary for forming flow rate estimation information, the general flow rate estimation information per se includes the correction information which has yet an indeterminate term, and hence, even when the measured data on the rotational speed N of the motor and the consumption current T of the motor of the objective blood pump which is implanted inside the body of the patient, and the attribute data Z of the blood of the patient is substituted into the general flow rate estimation information, the flow rate cannot be estimated.

(6) In the flow rate estimation method of a blood pump as mentioned in the above (1), the first step may includes a step which forms general flow rate estimation information including correction information by measuring flow rates of blood pumps using a blood flow meter when the rotational speed of the motor and the consumption current of the motor in a plurality of respective blood pumps, and the attribute data of a test liquid are respectively changed, and a step in which the rotational speed of the motor and the consumption current of the motor in the objective blood pump which is implanted inside the body of the patient, and the attribute data of the blood of the patient are measured and, the flow rate of the blood pump is measured using the blood flow meter, and the flow rate estimation information on the objective blood pump is formed based on the general flow rate estimation information by substituting the obtained measured data into the correction information.

By adopting such a method, in the same manner as the case of the flow rate estimation method of a blood pump described in the above (5), the formation of the flow rate estimation information which is originally cumbersome and time-consuming is divided into the former step which forms the general flow rate estimation information per se including the correction information and the latter step which forms the flow rate estimation information on the objective blood pump based on the general flow rate estimation information by substituting the measured data obtained from every objective blood pump into the correction information, wherein among these steps, the former step which is originally cumbersome and time-consuming is preliminarily performed using the plurality of blood pumps, and the latter step which is relatively less time-consuming is performed using the objective blood pump, and hence, in the same manner as the case of the flow rate estimation method of the blood pump described in the above (5), it becomes possible to easily form the flow rate estimation information as a whole.

Further, according to the flow rate estimation method of a blood pump described in the above (6), the flow rate estimation information on the objective blood pump is formed based on the general flow rate estimation information by substituting the measured data obtained using the objective blood pump which is implanted inside the body of the patient into the correction information, and hence, the flow rate estimation information is formed on the objective blood pump under an environment where it is actually used, whereby it is possible to effectively suppress the deterioration of the accuracy of the flow rate estimation result due to the difference of the environment where the blood pump is used.

Further, according to the flow rate estimation method of a blood pump described in the above (6), the flow rate estimation information on the objective blood pump is formed based on the general flow rate estimation information by substituting the measured data obtained using the objective blood pump which is implanted inside the body of the actual patient into the correction information and, thereafter, the flow rate estimation on the objective blood pump can be performed based on the flow rate estimation information. Accordingly, it becomes possible to effectively suppress the deterioration of the accuracy of the flow rate estimation result attributed to a change of the property of the blood pump along with a lapse of time.

Here, while the general flow rate estimation information including the correction information is, as also explained in the above (5), the information necessary for forming flow rate estimation information, the general flow rate estimation information per se includes the correction information which has yet an indeterminate term, and hence, even when the measured data on the rotational speed N of the motor and the consumption current I of the motor of the objective blood pump which is implanted inside the body of the patient, and the attribute data Z of the blood of the patient is substituted into the general flow rate estimation information, the flow rate cannot be estimated.

(7) In the flow rate estimation method of a blood pump as mentioned in the above (6), the blood flow meter may be a blood flow meter based on a thermodilution method, a blood flow meter based on a dye dilution method, an electromagnetic blood flow meter, an ultrasonic blood flow meter, a blood flow meter based on a transesophageal echocardiography, a blood flow meter based on a transthoracic echocardiography or a blood flow meter based on an electric impedance method may be used.

With the use of such a blood flow meter, the flow rate of the objective blood pump which is implanted inside the body of the patient can be measured, thus realizing the flow rate estimation of the blood pump with higher accuracy.

(8) In the flow rate estimation method of a blood pump as mentioned in the above (6), in the estimation of a flow rate of the blood pump in the second step, when the measurement of the flow rate of the objective blood pump with use of the blood flow meter is allowable, the flow rate estimation information on the objective blood pump may be updated by measuring the flow rate of the blood pump using the blood flow meter in performing the second step.

By adopting such a method, even when the property of the blood pump is changed along with a lapse of time, it becomes possible to properly update the flow rate estimation information to the newest flow rate estimation information, and hence, it becomes possible to further effectively suppress the deterioration of the accuracy of the flow rate estimation result attributed to a change of a property of the blood pump along with a lapse of time.

(9) In the flow rate estimation method of a blood pump as mentioned in any one of the above (5) to (8), the motor may particularly preferably be a DC motor.

In the DC motor, a relationship that the consumption current I and a shaft torque of the motor are proportional to each other is established. Further, a linear relationship is established between the flow rate Q of the blood pump and the shaft torque. Accordingly, a linear relationship is established between the flow rate Q of the blood pump and the consumption current I of the motor, thus facilitating the completion of the flow rate estimation information on the objective blood pump based on the general flow rate estimation information including the correction information.

(10) In the flow rate estimation method of a blood pump as mentioned in the above (1), the attribute data of the liquid, a test liquid or the blood of the patient may be constituted of viscosity and density of the liquid, the test liquid or the blood of the patient.

By adopting such a method, compared to a case in which only either one of viscosity or density is adopted as the attribute data of the liquid, the test liquid or the blood of the patient, it is possible to realize the flow rate estimation of the blood pump with higher accuracy.

(11) In the flow rate estimation method of a blood pump as mentioned in the above (10), "a hematocrit value of the blood of the patient" may be measured in the second step in place of measuring "viscosity and density of the blood of the patient", and the flow rate of the blood pump may be estimated using "converted viscosity and converted density" which are obtained by conversion based on a hematocrit value of the blood of the patient.

By adopting such a method, it is possible to perform the flow rate estimation of the blood pump using a simple method which only measures the hematocrit value without measuring viscosity or density of the blood of the patient.

(12) In the flow rate estimation method of a blood pump as mentioned in the above (1), the blood pump may particularly preferably be a blood pump which has a mechanical seal part for performing shaft-sealing of a rotational shaft of the motor.

In the blood pump having the mechanical seal part for performing the shaft-sealing of the rotational shaft of the motor (that is, for ensuring sealing between the pump part and the drive part) in this manner, the pump part and the drive part are well sealed from each other slidably, and hence, leaking of the blood into the drive part from the pump part can be suppressed as much as possible thus suppressing the generation of blood clot, whereby stopping of the blood pump or a change of an operational state of the blood pump can be suppressed as much as possible.

On the other hand, such a mechanical seal part requires the predetermined thrust load. Since there exists the relatively large individual difference with respect to this thrust load, there exists the relatively large individual difference also with respect to the property of the blood pump.

However, according to the flow rate estimation method of a blood pump of the present invention, the flow rate estimation information is formed for every blood pump, and hence, even when the relatively large individual difference exists with respect to the property of the blood pump, it is possible to eliminate the influence attributed to such individual difference, whereby it becomes possible to effectively suppress the deterioration of the accuracy of a result of the flow rate estimation attributed to the individual difference of the property of the blood pump.

Further, in such a mechanical seal part, the thrust load which is actually applied to a slide surface is relatively largely fluctuated due to an environment in which the blood pump is used such as the posture of the motor, and hence, the property of the blood pump is also relatively fluctuated.

However, according to the flow rate estimation method of a blood pump described in the above (6) of the present invention, the flow rate estimation information on the objective blood pump is formed based on the general flow rate estimation information by substituting the measured data obtained based on the objective blood pump which is implanted inside the body of the patient into the correction information, and hence, even when the property of the blood pump is relatively largely fluctuated due to the environment in which the blood pump is used, it is possible to effectively suppress the influence attributed to the fluctuation of the property of the blood pump, whereby it is possible to effectively suppress the deterioration of the accuracy of a result of the flow rate estimation attributed to the fluctuation of the property of the blood pump due to the environment in which the blood pump is used.

Further, the mechanical seal part includes the slide surface whose slide property is largely changed along with a lapse of time, and hence, the property of the blood pump is also largely changed along with a lapse of time.

However, according to the flow rate estimation method of a blood pump described in the above (6) of the present invention, the flow rate estimation information on the objective blood pump is formed based on the general flow rate estimation information by substituting the measured data obtained based on the objective blood pump which is implanted inside the body of the patient into the correction information, and hence, even when the property of the blood pump is relatively largely changed along with a lapse of time, it is possible to effectively suppress the influence attributed to the change of the property of the blood pump along with a lapse of time whereby it is possible to effectively suppress the deterioration of the accuracy of a result of the flow rate estimation attributed to the change of the property of the blood pump along with a lapse of time.

(13) A flow rate estimation method of a blood pump of the present invention estimates a flow rate Q of a blood pump which discharges blood using a rotational force of a motor as a driving power source based on a rotational speed N of the motor, a consumption current I of the motor and an attribute data Z of blood of a patient, and is characterized in that the rotational speed N of the motor and the consumption current I of the motor of the objective blood pump which is implanted inside the body of the patient, and the attribute data Z of the blood of the patient are measured, and a flow rate Q of the blood pump is estimated based on a preliminarily formed flow rate estimation information on the objective blood pump and the values of N, I and Z.

In this manner, according to the flow rate estimation method of a blood pump of the present invention, the rotational speed N of the motor and the consumption current I of the motor of the objective blood pump which is implanted inside the body of the patient, and the attribute data Z of the blood of the patient are measured, and the flow rate Q of the blood pump is estimated based on the preliminarily formed flow rate estimation information on the objective blood pump and these values N, I and Z, and hence, the deterioration of the accuracy of a result of the flow rate estimation attributed to the individual difference of the property of the blood pump can be eliminated thus achieving the object of the present invention.

(14) A flow rate estimation device of a blood pump of the present invention includes a function of estimating a flow rate of the blood pump by the flow rate estimation method of the blood pump as mentioned in the above (1) or (13), and is characterized in that the flow rate estimation device of the blood pump includes a flow rate estimation information storing part which stores the flow rate estimation information on the objective blood pump, and a flow rate estimation part which estimates the flow rate Q of the blood pump based on the flow rate estimation information stored in the flow rate estimation information storing part using the rotational speed N of the motor, the consumption current I of the motor and the attribute data Z of the blood of the patient.

In this manner, according to the flow rate estimation device of the blood pump of the present invention, the flow rate Q of the blood pump can be estimated based on the flow rate estimation information on the objective blood pump which is stored in the flow rate estimation information storing part using the rotational speed N of the motor, the consumption current I of the motor and attribute data Z of the blood of the patient, and hence, the deterioration of the accuracy of a result of the flow rate estimation attributed to the individual difference of the property of the blood pump can be eliminated thus achieving the object of the present invention.

(15) A blood pump system of the present invention includes a blood pump which discharges blood using a rotational force of a motor as a driving power source and an external controller which controls an operation of the blood pump, and is characterized in that the blood pump system further includes the flow rate estimation device of the blood pump as mentioned in the above (14).

In this manner, according to the blood pump system of the present invention, with the provision of the above-mentioned excellent flow rate estimation device of a blood pump, the deterioration of the accuracy of the flow rate estimation result attributed to the individual difference of the property of the blood pump can be eliminated, thus achieving the object of the present invention.

(16) A storage medium of the present invention is used for the flow rate estimation device of the blood pump as mentioned in the above (14), and is characterized in that the storage medium stores the general flow rate estimation information including the correction information or the flow rate estimation information.

In this manner, according to the present invention, with the provision of the storage medium, it becomes possible to realize the above-mentioned excellent flow rate estimation device of the blood pump, and hence, the deterioration of the accuracy of the flow rate estimation result attributed to the individual difference of the property of the blood pump can be eliminated, thus achieving the object of the present invention.

BEST MODE FOR CARRYING OUT THE INVENTION

Hereinafter, the explanation is made with respect to a flow rate estimation method of a blood pump, a flow rate estimation device of a blood pump, a blood pump system and a storage medium to which the present invention is applied in conjunction with embodiments shown in drawings.

Figure 1:
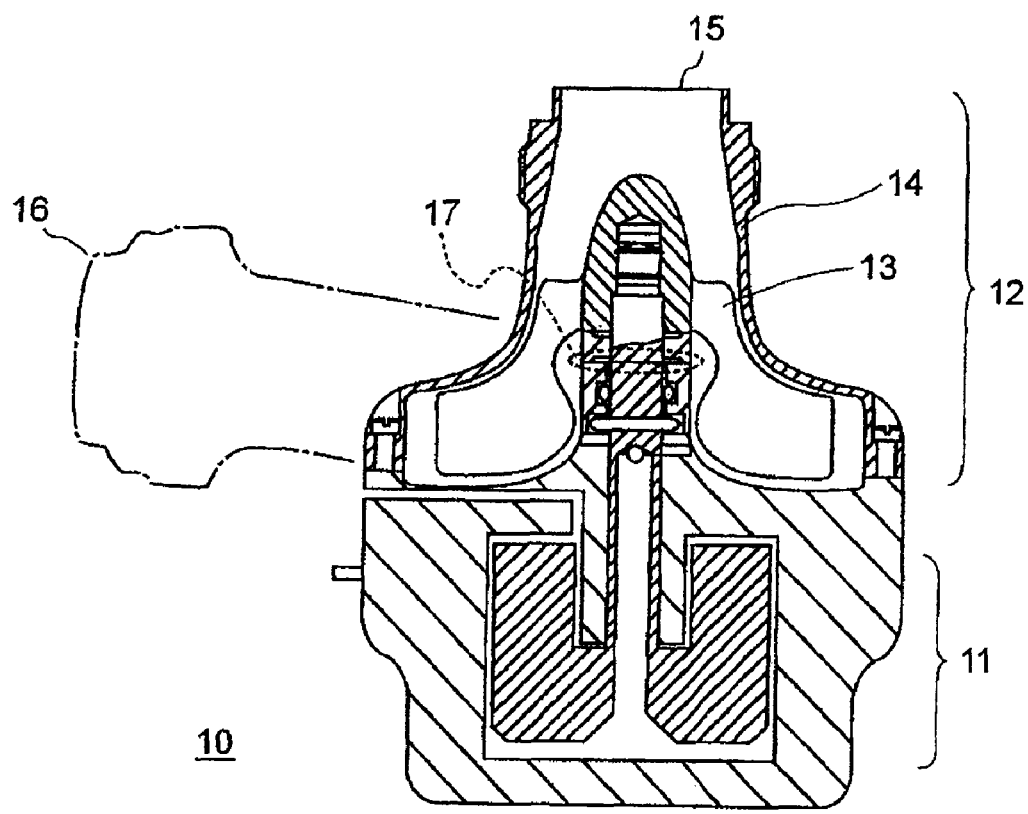
FIG. 1 is a cross-sectional view showing a blood pump.

First of all, prior to the explanation of the respective embodiments of the present invention, a blood pump which is used in respective embodiments of the present invention is explained in conjunction with FIG. 1.

FIG. 1 is a cross-sectional view showing the blood pump used in the respective embodiments of the present invention. The blood pump 10 includes, as shown in FIG. 1, a drive part 11 which has a cylindrical motor and a pump part 12 which is connected to the drive part 11. The pump part 12 includes an impeller 13 which is driven by way of a rotary shaft of the motor, and a pump casing 14 which is connected to the drive part 11 in a state that the pump casing 14 covers the impeller 13. Blood inside a left ventricle of a heart of a human body flows inside the pump casing 14 via an artificial blood vessel and an inlet port 15 and, after being imparted flow energy by the impeller 13, flows out to an aorta via an outlet port 16 formed in a side surface of the pump casing 14 and an artificial blood vessel.

In such a blood pump 10, a mechanical seal part 17 is arranged between the drive part 11 and the pump part 12. Accordingly, in the blood pump 10, the pump part 12 and the drive part 11 are slidably and favorably sealed from each other thus suppressing leaking of the blood from the pump part 12 to the drive part 11 as much as possible. As a result, the generation of a blood clot is suppressed as much as possible thus suppressing stopping of the blood pump and a change in an operation state of the blood pump as much as possible.

On the other hand, since the blood pump 10 is provided with the mechanical seal part 17, there exists the large individual difference, the large dependency on usage environment and a large change along with a lapse of time with respect to the property of the blood pump 10. In this manner, it is not easy to accurately perform the flow rate estimation of the blood pump 10. Accordingly, to properly perform the treatment of a serious heart disease using such a blood pump 10, a flow rate estimation method of a blood pump which can accurately perform the flow rate estimation of the blood pump is particularly strongly requested.

In the respective embodiments, as such a blood pump 10, a centrifugal blood pump which can ensure a larger blood flow rate compared to an axial blood flow motor is used. Further, in the respective embodiments, a DC motor is used as the motor for driving the impeller 13 of the blood pump 10.

[Embodiment 1]

The embodiment 1 is an embodiment with respect to the flow rate estimation method of a blood pump described in claim 6 of the present invention and a flow rate estimation device of the blood pump and a blood pump system to which the flow rate estimation method is applied.

Figure 2:
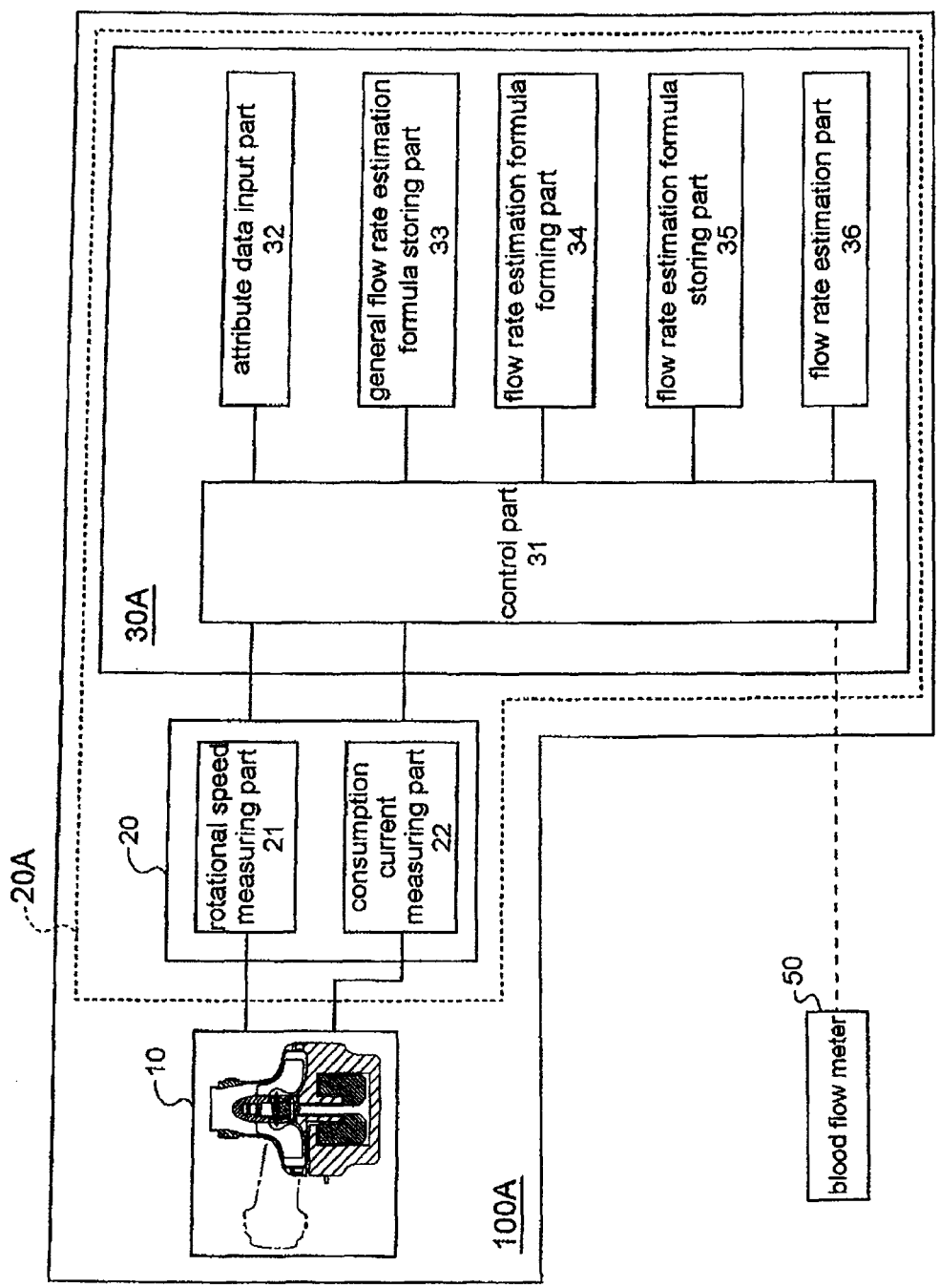
FIG. 2 is a view for explaining a blood pump system according to an embodiment 1.

FIG. 2 is a view for explaining the blood pump system according to the embodiment 1 of the present invention. The blood pump system 100A includes, as shown in FIG. 2, a blood pump (a objective blood pump) 10 which discharges blood using a rotational force of the motor as a driving power source, an external controller 20 which controls an operation of the objective blood pump 10, and a flow rate estimation device 30A of the blood pump for performing the flow rate estimation of the objective blood pump 10.

The external controller 20 includes a drive control part (not shown in the drawing) for driving the objective blood pump 10, and a circulation liquid control part (not shown in the drawing) for lubricating and cooling a mechanical seal part in the objective blood pump 10. The external controller 20 further includes, in addition to these parts, a rotational speed measuring part 21 for measuring a rotational speed N of the motor, and a consumption current measuring part 22 for measuring a consumption current I of the motor.

Here, in the blood pump system 100A according to the embodiment 1, the external controller 20 and the flow rate estimation device 30A of the blood pump are constituted as separate bodies from each other. However, the present invention is not limited to such a constitution and the external controller may have a flow rate estimation function of the blood pump (indicated by numeral 20A in FIG. 2).

The flow rate estimation device 30A of the blood pump includes an attribute data input part 32 for inputting attribute data of a test liquid or blood of a patient, a general flow rate estimation formula storing part 33 which stores a general flow rate estimation formula which is formed based on the rotational speed of the motor, the consumption current of the motor, the attribute data of the test liquid, and the flow rate of the blood pump and includes a correction term, a flow rate estimation formula forming part 34 which forms a flow rate estimation formula on the objective blood pump 10 by substituting measured data on the rotational speed $N_0$ of the motor, the consumption current $I_0$ of the motor, the attribute data $Z_0$ of the blood of the patient, and the flow rate $Q_0$ of the blood pump into the correction term, a flow rate estimation formula storing part 35 which stores the flow rate estimation formula formed by the flow rate estimation formula forming part 34, a flow rate estimation part 36 which estimates the flow rate Q of the blood pump based on the flow rate estimation formula stored in the flow rate estimation formula storing part 35 using the rotational speed N of the motor, the consumption current I of the motor, and the attribute data Z of the blood of the patient, and a control part 31 which controls these parts. Further, the flow rate estimation device 30A includes a connection part (not shown in the drawing), which connects the flow rate estimation device 30A with a blood flow meter 50 which measures the flow rate of the objective blood pump 10.

Here, the flow rate estimation device 30A of the blood pump according to the embodiment 1 includes the flow rate estimation formula forming part 34 and the flow rate estimation formula storing part 35. However, the present invention is not limited to such a constitution, and the flow rate estimation device 30A may also include a flow rate estimation device of the blood pump which is provided with neither the flow rate estimation formula forming part 34 nor the flow rate estimation formula storing part 35. In this case, the flow rate estimation part 36 forms the flow rate estimation formula of the objective blood pump 10 based on the general flow rate estimation formula which includes the correction term stored in the general flow rate estimation formula storing part 33 and the measured data consisting of the measured rotational speed $N_0$ of the motor, the measured consumption current $I_0$ of the motor, the measured attribute data $Z_0$ of the blood of the patient, and the flow rate $Q_0$ of the blood pump, for every time the flow rate estimation is performed, and estimates the flow rate Q of the blood pump in the objective blood pump 10 based on the flow rate estimation formula of the objective blood pump 10. Here, in this case, the flow rate estimation device 30A may include a measured data storing part which stores the above-mentioned measured data.

Figure 3:
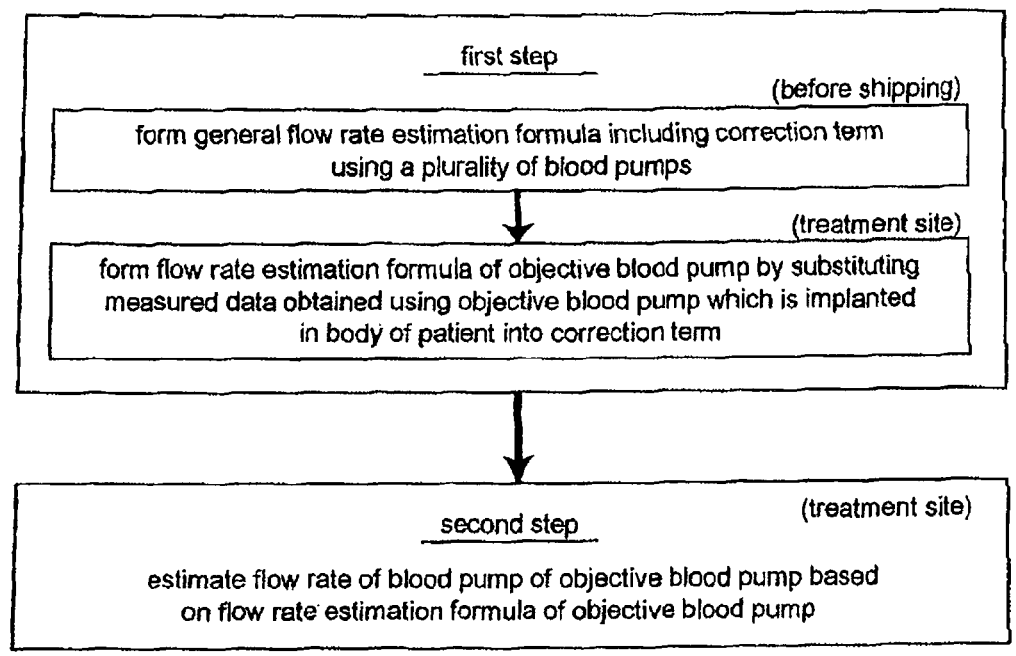
FIG. 3 is a view for explaining a flow rate estimation method of a blood pump according to the embodiment 1.

FIG. 3 is a view for explaining the flow rate estimation method of the blood pump according to the embodiment 1. The flow rate estimation method of the blood pump according to the embodiment 1 is constituted of, as shown in FIG. 3, a first step and a second step.

(First Step)

The first step is constituted of a step in which the general flow rate estimation formula including the correction term is formed and a step in which the flow rate estimation formula of the objective blood pump 10 is formed.

Out of these steps, the step for forming the general flow rate estimation formula including the correction term is a step in which the plurality of blood pumps having the same standard and specification as the objective blood pump 10 is prepared and flow rates of the blood pumps are measured using flow meters (not shown in the drawing in FIG. 2) when rotational speeds of the motors, consumption currents of the motors of the plurality of respective blood pumps and the attribute data of the test liquid are respectively changed, and the general flow rate estimation formula including the correction term on which the individual difference among the plurality of blood pumps is reflected is formed based on the measured data.

As the test liquid, for example, water or a mixed solution of water and glycerin which is adjusted to a plurality of viscosities are used. As the attribute data of the test liquid, the viscosity μ and the density ρ are used.

Further, the step for forming the flow rate estimation formula of the objective blood pump 10 is a step in which a rotational speed $N_0$ of the motor, a consumption current $I_0$ of the motor of the objective blood pump 10 implanted inside the body of the patient and the attribute data $Z_0$ of the blood of the patient are measured (at least one time) and, at the same time, a flow rate $Q_0$ of the blood pump at this point of time is measured using the blood flow meter 50, the obtained measured data is substituted into the correction term, whereby the flow rate estimation formula of the objective blood pump 10 is formed based on the general flow rate estimation information. As the attribute data of the blood of the patient, the viscosity μ and the density ρ are used.

Among these steps, the step for forming the general flow rate estimation formula is usually collectively performed using a plurality of blood pumps before shipping the objective blood pump 10.

Further, among these steps, the step for forming the flow rate estimation formula of the objective blood pump 10 is performed using the objective blood pump 10 after implanting the objective blood pump 10 inside the body of the patient.

(Step for Forming General Flow Rate Estimation Formula Including Correction Term in First Step)

This step is a step in which a plurality of blood pumps is prepared, the flow rates of the blood pumps are measured using a flow meter (a flow meter for industrial use or the like) when the rotational speeds of the motors and the consumption currents of the motors of the plurality of respective blood pumps, and the attribute data of the test liquid are respectively changed, and the general flow rate estimation formula including the correction term is formed based on the measured values.

Figure 4:
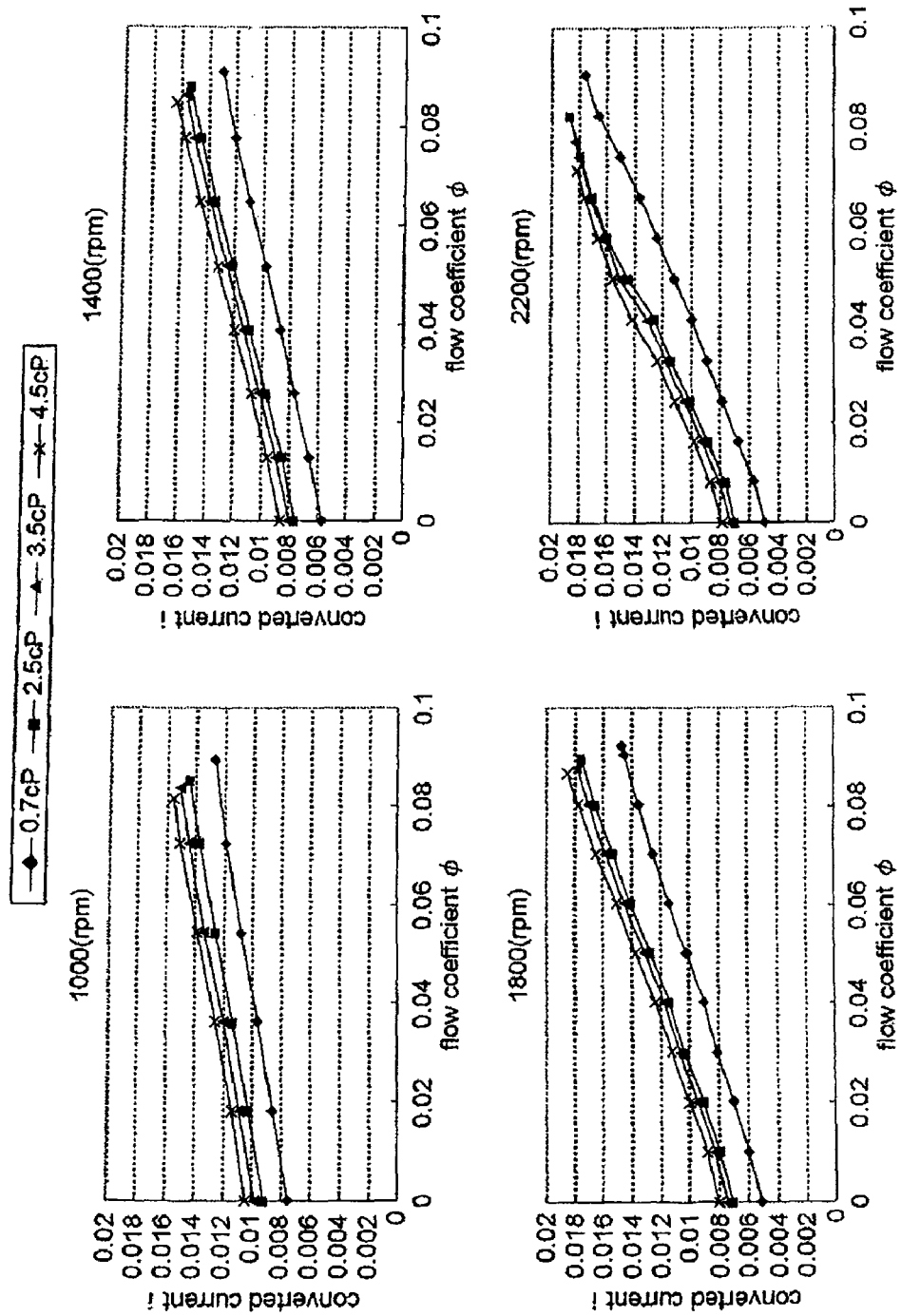
FIG. 4 is a view showing a relationship between a flow coefficient and a converted current for every rotational speed of a motor.

FIG. 4 is a view which shows a relationship between a flow coefficient φ obtained by standardizing the flow rate Q of the blood pump of the blood pump system according to the embodiment 1 (=the flow rate Q of the blood pump/(the flow path area A·the impeller peripheral speed u)) and a converted current ι obtained by standardizing the consumption current I of the motor (=consumption current I of the motor/(density ρ of the test liquid×the angular velocity $\omega^2$)) for every viscosity μ of the test liquid (0.7 cP, 2.5 cP, 3.5 cP, 4.5 cP) and the rotational speed N of the motor (1000 rpm, 1400 rpm, 1800 rpm, 2200 rpm).

In the blood pump system 100A, as shown in FIG. 4, the flow coefficient φ and the converted current ι have an approximately linear relationship, and hence, it is possible to form a relationship formula (1) for every rotational speed N of the motor by approximating the linear relationship to a linear equation based on least square. The respective coefficients here can be expressed as functions of the viscosity μ of the test liquid.

$$\iota = (C \cdot \mu + D)\phi + (E \cdot \mu + F) \qquad (1)$$

Here, the coefficients C, D, E, and F can be expressed as functions of the rotational speed N of the motor. For example, the coefficients C, D, E, and F can be expressed as following functions.

$$C(N) = -1.12 \times 10^{-11} N^3 + 4.83 \times 10^{-8} N^2 - 6.32 \times 10^{-5} N + 2.76 \times 10^{-2}$$

$$D(N) = 6.57 \times 10^{-5} N - 9.39 \times 10^{-3}$$

$$E(N) = 8.85 \times 10^{-8} N + 6.34 \times 10^{-4}$$

$$F(N) = 2.00 \times 10^{-9} N^2 - 8.85 \times 10^{-6} N + 1.38 \times 10^{-2}$$

Then, by developing the relationship formula (1), it is possible to obtain a basic estimation formula (2) described below.

$$Q = [I \times 10^6 / \rho \omega^2 - (E(N)\mu + F(N))] \cdot [A u / (C(N)\mu + D(N))] \qquad (2)$$

Figure 5:
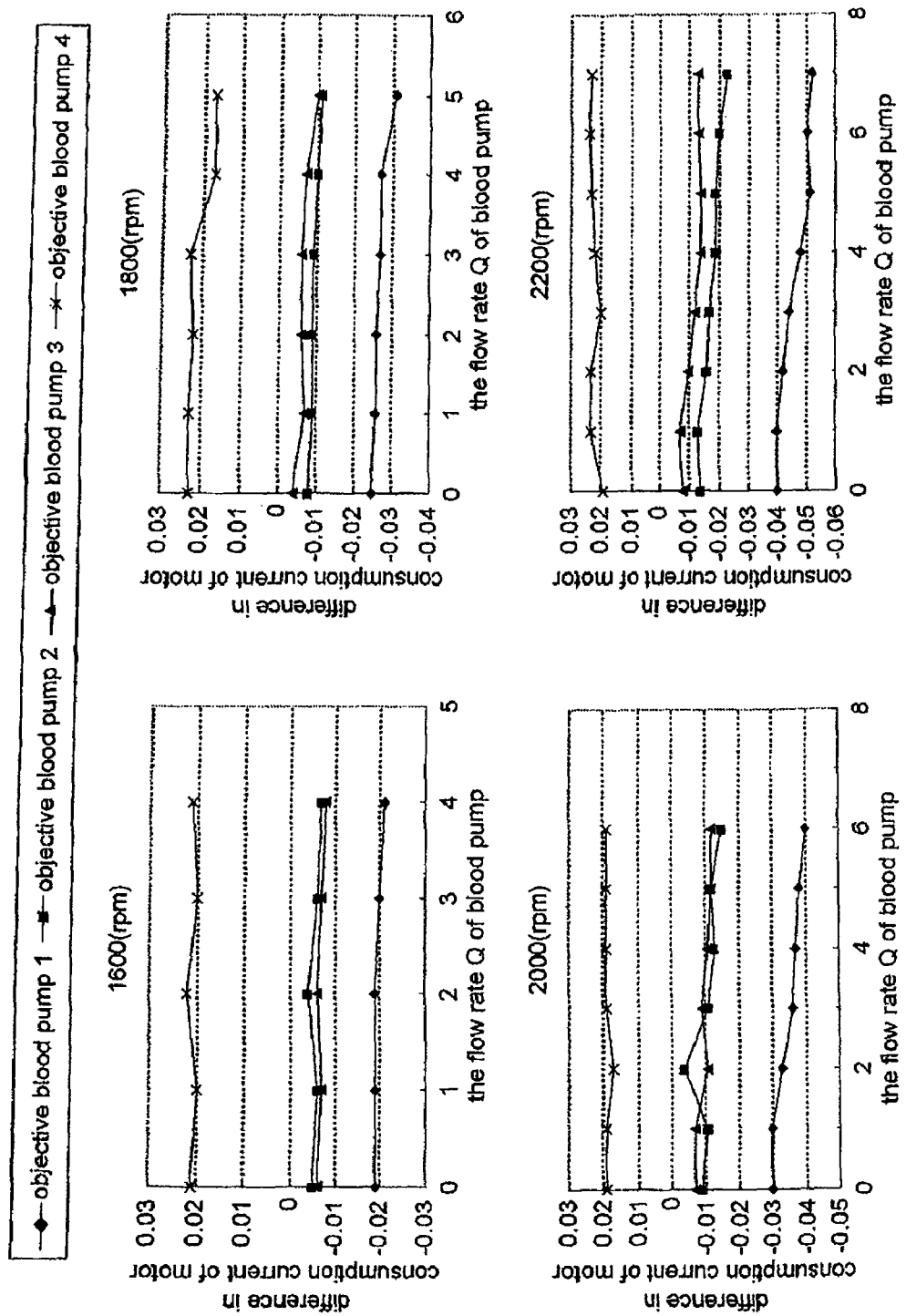
FIG. 5 is a view showing the difference between the objective blood pump and an arbitrary blood pump with respect to a consumption current of the motor when a flow rate of a blood pump is changed for every rotational speed of the motor.

FIG. 5 is a view showing the difference between the objective blood pump and the arbitrary blood pump in the consumption current of the motor for every rotational speed of the motor when the flow rate of the blood pump is changed. As shown in FIG. 5, it is understood that the difference between the objective blood pump 10 and the arbitrary blood pump in the consumption current of the motor is substantially fixed irrespective of the flow rate of the objective blood pump 10 at any rotational speed.

Figure 6:
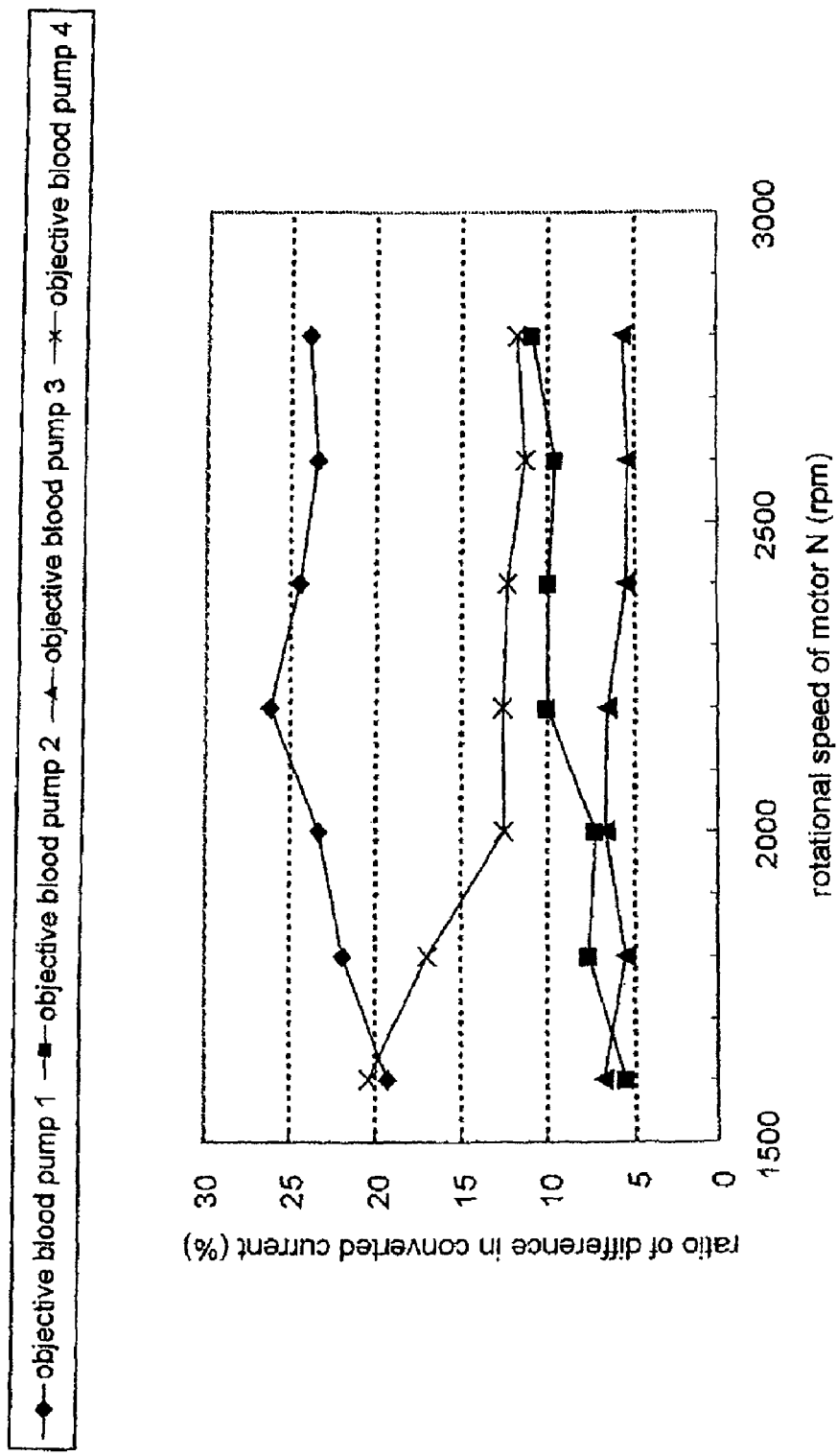
FIG. 6 is a view showing the difference (ratio) between the objective blood pump and an arbitrary blood pump with respect to a consumption current of the motor when the rotational speed of the motor is changed.

FIG. 6 is a view showing the difference (ratio) between the objective blood pump and the arbitrary blood pump in the consumption current of the motor when the rotational speed of the motor is changed. As shown in FIG. 6, it is understood that the difference (ratio) between the objective blood pump 10 and the arbitrary blood pump in the consumption current of the motor is substantially fixed irrespective of the rotational speed of the motor.

From these findings, it is understood that the flow rate Q of the blood pump assumes a value which is offset by a predetermined value from a flow rate of the arbitrary blood pump irrespective of the rotational speed of the motor and the consumption current of the motor. Accordingly, by measuring this offset quantity using the objective blood pump 10 and by adding the correction corresponding to the offset quantity to the estimation result obtained from the basic estimation formula (2), it is possible to obtain the more accurate result of flow rate estimation in the objective blood pump 10. Accordingly, to facilitate the later correction treatment in the step for forming the flow rate estimation formula of the objective blood pump, the following general flow rate estimation formula (3) which incorporates a correction term in the basic estimation formula (2) is formed.

$$Q = \{I \times 10^6 / \rho \omega^2 - [E(N)\mu + F(N) + ((*-A(\mu^*)\phi^*) - B(\mu^*))/B(\mu^*) \times (E(N)\mu + F(N))]\} \cdot [Au / (C(N)\mu + D(N))] \qquad (3)$$

Here, $i^*$, $\mu^*$, $\phi^*$ are variable terms into which measured data $i_0$, $\mu_0$, $\phi_0$ which are measured in the later step are inserted.

In the blood pump system 100A, the general flow rate estimation formula (3) including the correction term which is formed in this manner may be stored in the general flow rate estimation formula storing part 33.

(Step for Forming the Flow Rate Estimation Formula of Objective Blood Pump in First Step)

This step is a step in which the rotational speed of the motor and the consumption current of the motor of the objective blood pump 10 implanted inside the body of the patient and the attribute data of the blood of the patient are measured and, at the same time, the flow rate of the blood pump is measured using the blood flow meter 50, and the flow rate estimation formula of the objective blood pump is formed from the general flow rate estimation formula (3) by substituting the obtained data into the correction term.

As has been described above, the flow rate Q of the blood pump assumes a value which is offset by the predetermined value from the flow rate of the arbitrary blood pump irrespective of the rotational speed of the motor and the consumption current of the motor. Accordingly, the rotational speed $N_0$ of the motor and the consumption current $I_0$ of the motor of the objective blood pump 10 implanted inside the body of the patient, and the attribute data $Z_0$ of the blood of the patient (at least one time) are measured, and at the same time the flow rate $Q_0$ of the blood pump at this point of time is measured using the blood flow meter 50, whereby the flow rate estimation formula (4) of the objective blood pump 10 is formed by substituting the obtained measured data into the correction term of the general flow rate estimation formula (3).

$$Q = \{I \times 10^6 / \rho \omega^2 - [E(N)\mu + F(N) + ((i_0 - A(\mu_0)\phi_0) - B(\mu_0))/B(\mu_0) \times (E(N)\mu + F(N))]\} \cdot [Au / (C(N)\mu + D(N))] \qquad (4)$$

The formation of the flow rate estimation formula (4) of the objective blood pump 10 is performed by the flow rate estimation formula forming part 34. Then, the obtained flow rate estimation formula (4) is stored in a flow rate estimation formula storing part 35.

(Second Step)

The second step is a step in which the rotational speed N of the motor and the consumption current I of the motor of the objective blood pump 10 implanted inside the body of the patient, and the attribute data Z of the blood of the patient are measured, and the flow rate Q of the blood pump is estimated based on the flow rate estimation formula (4) which is stored in the flow rate estimation formula storing part 35 and these values N, I and Z. As the attribute data of the blood of the patient, the viscosity μ and the density ρ are used.

Here, with respect to the rotational speed N of the motor and the consumption current I of the motor, the measured data is obtained by performing the automatic measurement every time the flow rate estimation is performed, while with respect to the attribute data Z (μ, φ) of the blood of the patient, the measured data is obtained by inputting the attribute data using the attribute data input part 32.

Figure 7:
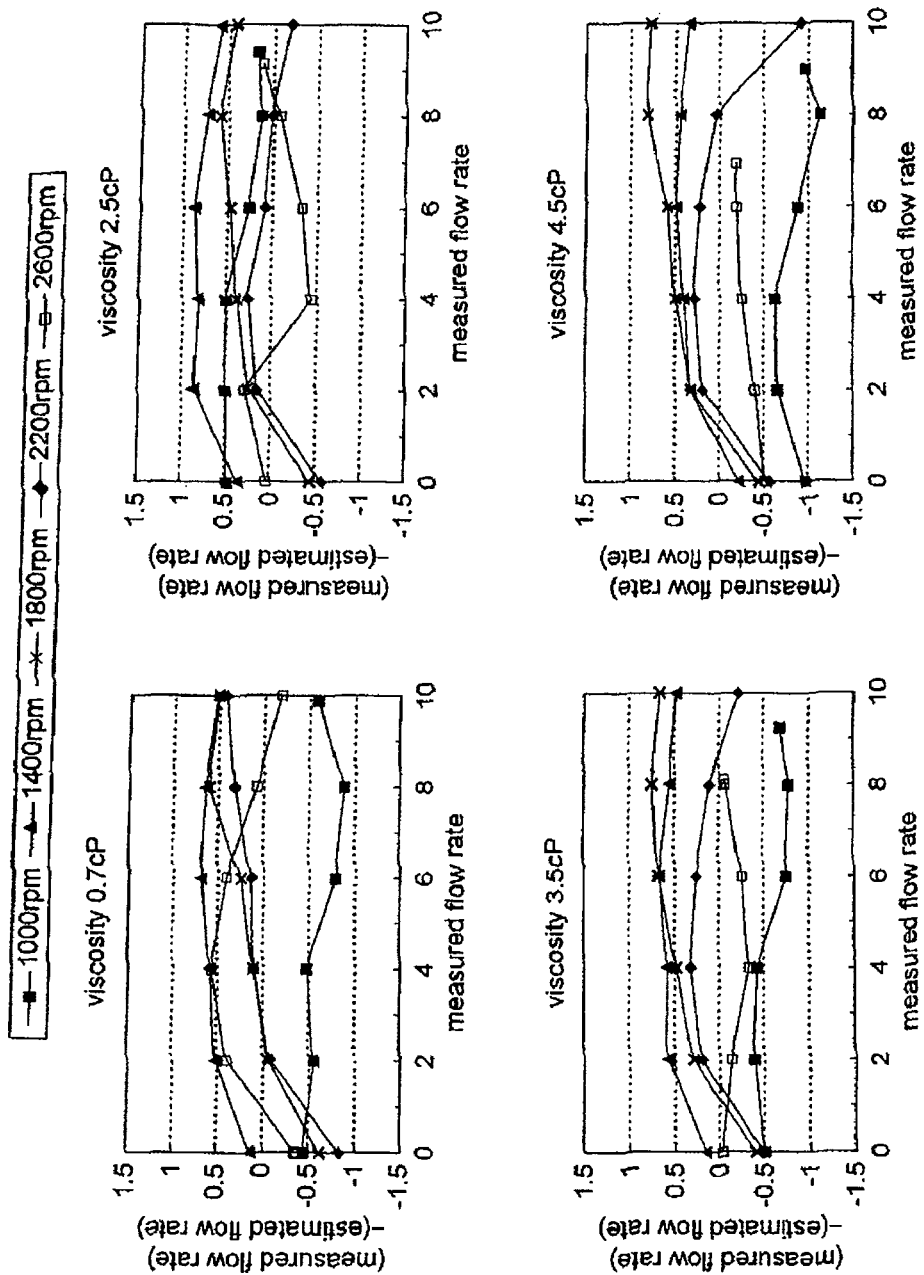
FIG. 7 is a view showing the difference between an estimated flow rate and a measured flow rate of the objective blood pump.

FIG. 7 is a view showing the difference between the estimated flow rate of the objective blood pump obtained by estimation using the flow rate estimation formula (4) and the measured flow rate obtained by actually measuring the flow rate using the flow meter under proper conditions. Such a difference is, as shown in FIG. 7, when the flow rate of the blood pump is within a range of 10 liters/min or less, set to a value smaller than a target value (±1 liter/min) which is considered as an allowable range clinically. It is confirmed that the flow rate of the blood pump can be accurately estimated according to the flow rate estimation method of the blood pump of the embodiment 1.

Although the flow rate estimation method of the blood pump according to the embodiment 1 has been explained heretofore, by using the flow rate estimation method of the blood pump according to the embodiment 1, in the first step, the flow rate estimation formula (4) is formed with respect to the objective blood pump 10 on which the flow rate estimation is performed, and in the second step, the flow rate estimation is performed with respect to the objective blood pump 10 based on the flow rate estimation formula (4), and hence, the deterioration of the accuracy of the result of the flow rate estimation due to the individual difference of the property of the blood pump can be effectively suppressed.

Further, according to the flow rate estimation method of a blood pump of the embodiment 1, the flow rate estimation formula (4) is formed by using the objective blood pump 10 which is implanted inside the body of the patient, and hence, it is possible to form the flow rate estimation formula (4) with respect to the objective blood pump 10 under the environment in which the blood pump 10 is actually used whereby the deterioration of the accuracy of the flow rate estimation result attributed to the difference of the environment in which the blood pump is used can be effectively suppressed.

Further, according to the flow rate estimation method of a blood pump of the embodiment 1, the flow rate estimation formula (4) is formed using the objective blood pump 10 implanted inside the body of the patient and, thereafter, the flow rate estimation of the objective blood pump 10 can be performed based on the flow rate estimation formula (4), and hence, it is possible to effectively prevent the deterioration of accuracy of the flow rate estimation result attributed to the change of the property of the blood pump along with a lapse of time.

Further, according to the flow rate estimation method of a blood pump of the embodiment 1, the formation of the flow rate estimation formula (4) which is originally cumbersome and time-consuming is divided into the step which forms the general flow rate estimation formula (3) including the correction term and the step which forms the flow rate estimation formula (4) on the objective blood pump by substituting the measured data obtained for every objective blood pump into the correction term, wherein among these steps, the former step which is originally cumbersome and time-consuming is performed preliminarily using a plurality of blood pumps, and the latter step which is relatively less time-consuming is performed using the objective blood pump whereby it is possible to further easily form the flow rate estimation formula (4) as a whole.

In the flow rate estimation method of a blood pump according to the embodiment 1, in estimating the flow rate of the blood pump in step 2, when it is possible to measure the flow rate of the objective blood pump 10 using the blood flow meter 50, the flow rate of the objective blood pump 10 is measured using the flow meter 50 at the time of performing the second step, and hence, the flow rate estimation formula (4) can be always updated to the newest flow rate estimation formula (4). Accordingly, even when the property of the blood pump is changed along with a lapse of time, the flow rate estimation of the blood pump can be performed using the newest flow rate estimation formula (4), whereby it is possible to further effectively suppress the deterioration of accuracy of the result of the flow rate estimation attributed to the change of the property of the blood pump along with a lapse of time.

In the flow rate estimation method of a blood pump according to the embodiment 1, as the blood flow meter 50, a blood flow meter based on a thermodilution method is used. In this case, by adjusting the rotational speed of the motor of the objective blood pump 10 such that the whole blood in the body circulatory system passes through the objective blood pump 10 by reference to a blood monitor, an ultrasonic diagnosis device or the like, the blood flow rate obtained by blood flow meter 50 becomes substantially equal to the blood flow rate of the objective blood pump 10, and hence, it is possible to perform the flow rate estimation of the blood pump with higher accuracy. Here, in performing the measurement of the flow rate using the blood flow meter 50, it is necessary to implant a catheter inside the body of the patient. However, the implanting of the catheter for a certain period after an operation to implant the blood pump is usually performed, and hence, it isn't further invasive to the patient.

In the flow rate estimation method of a blood pump according to the embodiment 1, viscosity and density are used as the attribute data of the test liquid and the blood of the patient. Accordingly, compared to a case in which either one of viscosity or density is adopted, it is possible to perform the flow rate estimation of the blood pump with higher accuracy.

In the flow rate estimation method of a blood pump according to the embodiment 1, in place of measuring viscosity and density of the blood of the patient in the second step, a hematocrit value may be measured, and the flow rate of the blood pump may be estimated using converted viscosity and converted density obtained by converting the hematocrit value. By adopting such a method, it is possible to perform the flow rate estimation of the blood pump using a simple method which measures only the hematocrit value without measuring viscosity and density of the blood of the patient.

Figure 8:
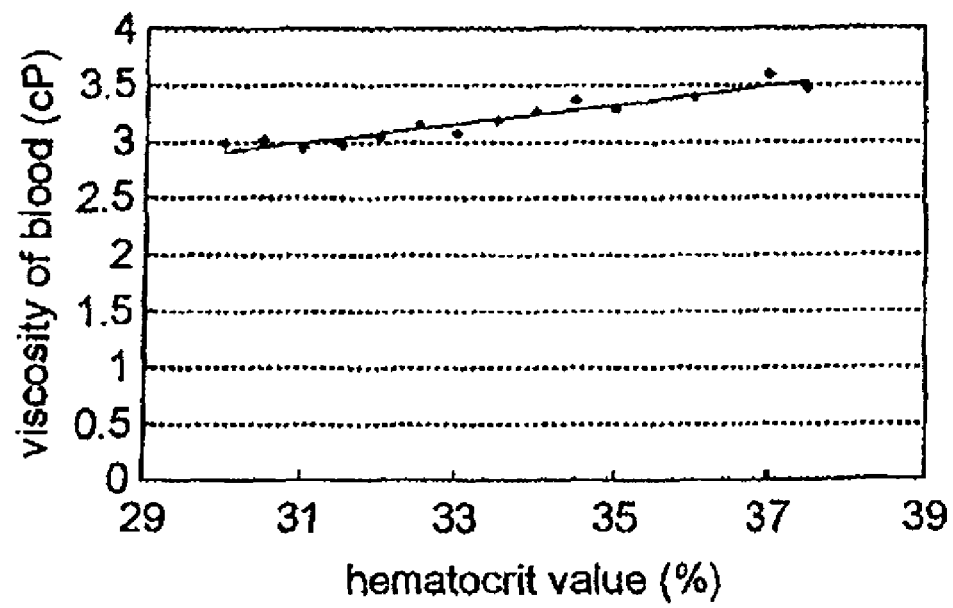
FIG. 8 is a view showing a relationship between a hematocrit value and viscosity of blood.
Figure 9:
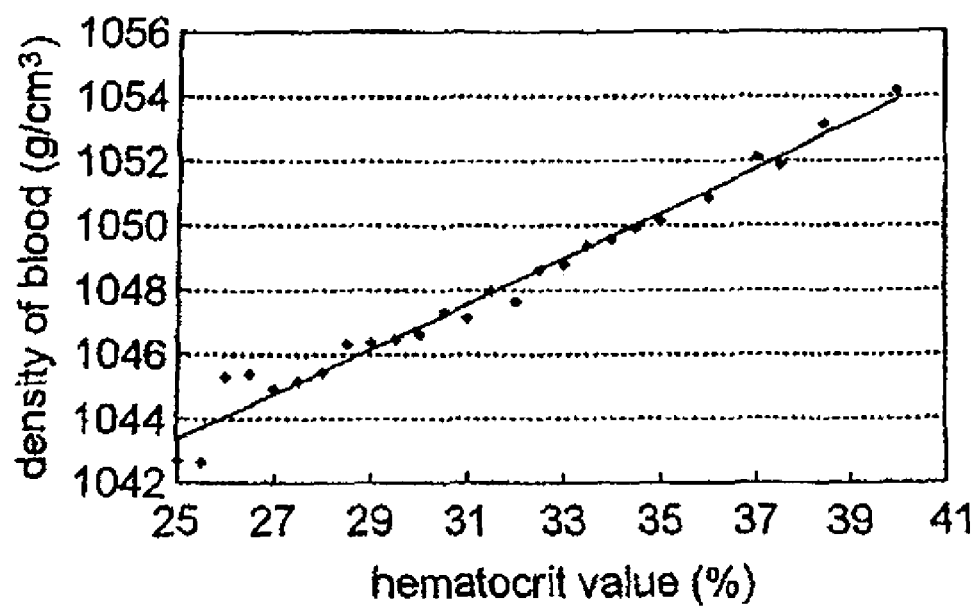
FIG. 9 is a view showing a relationship between a hematocrit value and density of blood.

FIG. 8 is a view showing a relationship between the hematocrit value of the blood and the viscosity of the blood, while FIG. 9 is a view showing a relationship between the hematocrit value of the blood and the density of the blood. As shown in FIG. 8 and FIG. 9, between the hematocrit value of the blood and the viscosity and the density of the blood, a strong correlation exists. That is, also with respect to the blood of the patient, there exists a strong correlation between the hematocrit value Ht of the blood of the patient and the viscosity $\mu$ and the density $\rho$ of the blood of the patient, and hence, in place of measuring the viscosity $\mu$ and the density $\rho$ of the blood of the patient, the viscosity $\mu$ and the density $\rho$ of the blood of the patient can be obtained by measuring the hematocrit value Ht of the blood of the patient and by converting the hematocrit value Ht of the blood of the patient to the viscosity $\mu$ and the density $\rho$ of the blood of the patient.

As has been explained above, the flow rate estimation method of a blood pump according to the embodiment 1 is an excellent flow rate estimation method of a blood pump, which can effectively suppress the deterioration of the accuracy of the flow rate estimation result attributed to the individual difference of the blood pump, the dependency on usage environment, or the change along with a lapse of time. Accordingly, with the use of such an excellent flow rate estimation method of a blood pump, it is possible to perform treatment using the implantable blood pump more properly.

Further, the flow rate estimation device 30A of a blood pump according to the embodiment 1 can perform the flow rate estimation of the blood pump using the excellent flow rate estimation method of a blood pump, which can effectively suppress the deterioration of the accuracy of the flow rate estimation result attributed to the individual difference, the dependency on usage environment, or the change along with a lapse of time of the blood pump described above. Accordingly, with the use of such an excellent flow rate estimation device 30A of the blood pump, it is possible to perform treatment using the implantable blood pump more properly.

Further, the blood pump system 100A according to the embodiment 1 is a blood pump system provided with the excellent flow rate estimation device 30A of a blood pump, which can effectively suppress the deterioration of the accuracy of the flow rate estimation result attributed to the individual difference, the dependency on usage environment, or the change along with a lapse of time of the blood pump described above. Accordingly, with the use of such an excellent blood pump system 100A, it is possible to perform treatment using the implantable blood pump more properly.

Still further, the general flow rate estimation formula to be stored in the general flow rate estimation formula storing part 33 and the flow rate estimation formula of the objective blood pump 10 to be stored in the flow rate estimation formula storing part 35 in the flow rate estimation device 30A of the blood pump according to the embodiment 1 may be stored in a predetermined storage medium (for example, a CD-ROM). In this case, by allowing a computer system to read the flow rate estimation formulae stored in the storage medium, it is possible to use the computer system as the flow rate estimation device 30A of the blood pump. Accordingly, with the use of such a storage medium, it is possible to perform the treatment using the implantable blood pump more properly.

[Embodiment 2]

Embodiment 2 is an embodiment with respect to a flow rate estimation method of a blood pump described in claim 5 of the present invention and a flow rate estimation device of a blood pump and a blood pump system to which the flow rate estimation method of a blood pump is applied.

Figure 10:
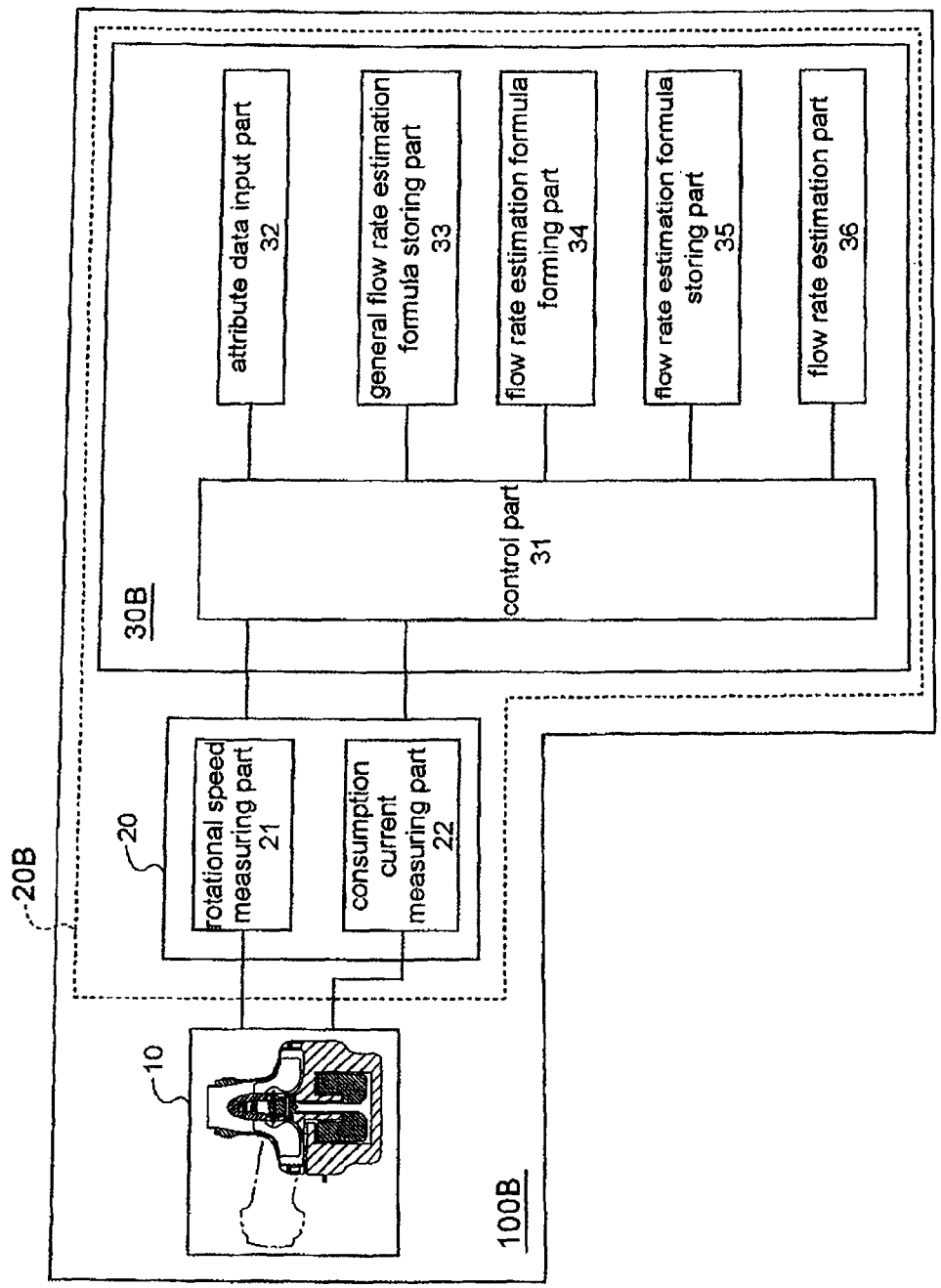
FIG. 10 is a view for explaining a blood pump system according to an embodiment 2.

FIG. 10 is a view for explaining a blood pump system according to the embodiment 2 of the present invention. The blood pump system 100B (and the flow rate estimation device 30B of the blood pump) according to the embodiment 2 has, as shown in FIG. 10, the same constitution as the blood pump system 100A (and the flow rate estimation device 30A of the blood pump) according to the embodiment 1 except for the point that the embodiment 2 is not provided with the connection part with the blood flow meter.

Figure 11:
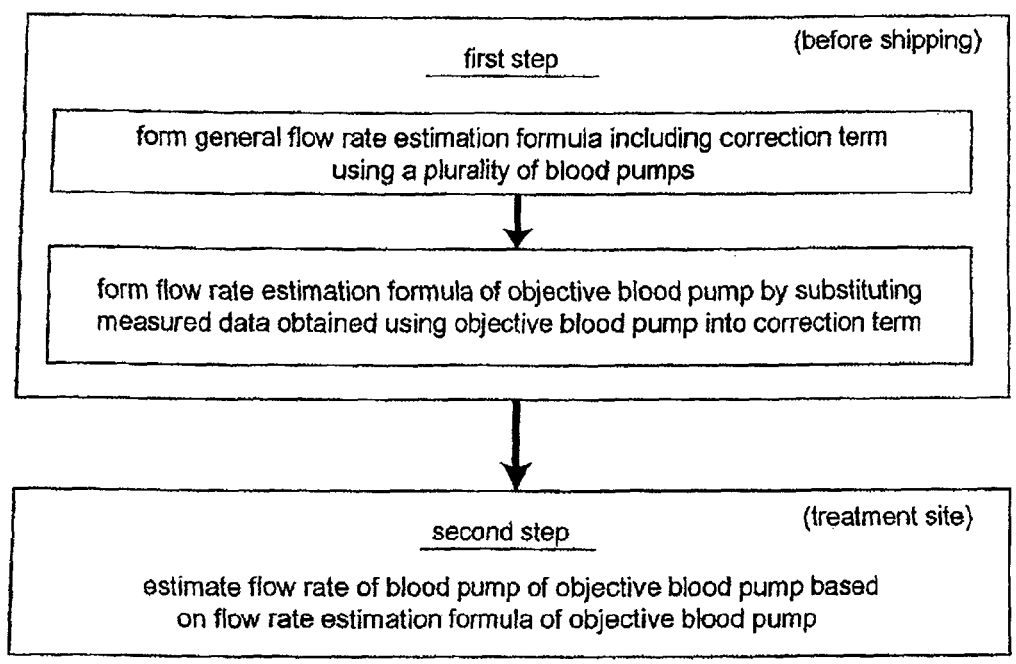
FIG. 11 is a view for explaining a flow rate estimation method of a blood pump according to the embodiment 2.

FIG. 11 is a view for explaining a flow rate estimation method of the blood pump according to the embodiment 2. The flow rate estimation method of the blood pump according to the embodiment 2 is constituted of a first step and a second step as shown in FIG. 11.

(First Step)

The first step is constituted of a step in which the general flow rate estimation formula including the correction term is formed and a step in which the flow rate estimation formula of the objective blood pump 10 is formed.

Out of these steps, the step which forms the general flow rate estimation formula including the correction term is a step in which the plurality of blood pumps having the same standard and specification as the objective blood pump 10 is prepared and flow rates of the blood pumps are measured using flow meters (such as flow meters for industrial use) when rotational speeds of the motors, consumption currents of the motors of the plurality of respective blood pumps and the attribute data of the test liquid are respectively changed, whereby the general flow rate estimation formula including the correction term is formed.

As the test liquid, for example, water and a mixed solution of water and glycerin which is adjusted to a plurality of viscosities are used. As the attribute data of the test liquid, the viscosity $\mu$ and the density $\rho$ are used. That is, the test liquid is used in the same manner as the flow estimation method of the blood pump according to the embodiment 1.

Further, the step for forming the flow rate estimation formula of the objective blood pump 10 is a step in which a rotational speed of the motor, a consumption current of the motor of the objective blood pump 10, and the attribute data of the test liquid are measured and, at the same time, a flow rate of the blood pump is measured using the flow meter, and the flow rate estimation formula of the objective blood pump 10 is formed based on the general flow rate estimation information by substituting the obtained data into the correction term. As the test liquid, for example, water or a mixed solution of water and glycerin is used. It is particularly preferable to use a solution which is adjusted to have the viscosity substantially equal to the viscosity of the blood. As the attribute data of the test liquid, the viscosity $\mu$ and the density $\rho$ are used.

Among these steps, the step for forming the general flow rate estimation formula including the correction term is, in the same manner as the embodiment 1, collectively performed using a plurality of blood pumps before shipping the objective blood pump 10.

Further, among these steps, the step for forming the flow rate estimation formula of the objective blood pump 10 is performed, different from the embodiment 1, using the objective blood pump 10 before shipping the objective blood pump 10.

(Second Step)

The second step is a step in which the rotational speed N of the motor and the consumption current I of the motor of the objective blood pump 10 implanted inside the body of the patient, and the attribute data Z of the blood of the patient are measured, and the flow rate Q of the blood pump of the objective blood pump 10 is estimated based on the flow rate estimation formula of the objective blood pump 10 which is formed previously and these values N, I and Z. The second step is substantially equal to the second step of the embodiment 1. As the attribute data of the blood of the patient, the viscosity $\mu$ and the density $\rho$ are used.

The second step is performed after implanting the objective blood pump 10 inside the body of the patient in the same manner as the embodiment 1.

In this manner, according to the flow rate estimation method of the blood pump of the embodiment 2, in the same manner as the embodiment 1, in the first step, the flow rate estimation formula is formed with respect to the objective blood pump 10 on which the flow rate estimation is performed, while in the second step, the flow rate estimation is performed with respect to the objective blood pump 10 based on this flow rate estimation formula, and hence, it is possible to effectively suppress the deterioration of the accuracy of the flow rate estimation result attributed to the individual difference of the property of the blood pump.

Further, according to the flow rate estimation method of the blood pump of the embodiment 2, different from the case of the flow rate estimation method of a blood pump according to the embodiment 1, the flow rate estimation formula is formed using the test liquid, and hence, it is possible to finish the cumbersome and time-consuming first step before shipping.

Further, since the cumbersome and time-consuming first step can be performed before implanting the objective blood pump 10 inside the body of the patient, a burden imposed on the patient is not increased.

Still further, by performing the formation of the flow rate estimation formula for every objective blood pump, it may be possible to perform the flow rate estimation with respect to the objective blood pump with higher accuracy immediately after implanting the objective blood pump inside the body of the patient.

In the flow rate estimation method of a blood pump according to the embodiment 2, the originally cumbersome and time-consuming formation of the flow rate estimation formula in the first step is divided into the step which forms the general flow rate estimation formula including the correction term and the step which forms the flow rate estimation formula with respect to the objective blood pump, and the latter step is performed before shipping, and hence, compared to the flow rate estimation method of the blood pump according to the embodiment 1, the flow rate estimation formula can be further easily formed as a whole.

As has been explained above, the flow rate estimation method of a blood pump according to the embodiment 2 is an excellent flow rate estimation method of a blood pump, which can effectively suppress the deterioration of the accuracy of the result of flow rate estimation attributed to the individual difference of the blood pump as mentioned above. Accordingly, also with the use of such an excellent flow rate estimation method of a blood pump, it is possible to perform treatment using the implantable blood pump more properly.

Further, the flow rate estimation device 30B of a blood pump according to the embodiment 2 can perform the flow rate estimation of the blood pump using the excellent flow rate estimation method of a blood pump, which can effectively suppress the deterioration of the accuracy of the result of the flow rate estimation attributed to the individual difference of the blood pump as described above. Accordingly, also with the use of such an excellent flow rate estimation device 30B of the blood pump, it is possible to perform treatment using the implantable blood pump more properly.

Further, the blood pump system 100B according to the embodiment 2 is a blood pump system provided with the excellent flow rate estimation device 30B of the blood pump, which can effectively suppress the deterioration of the accuracy of the flow rate estimation result attributed to the individual difference of the blood pump as described above. Accordingly, also with the use of such an excellent blood pump system 100B, it is possible to perform treatment using the implantable blood pump more properly.

Still further, the general flow rate estimation formula to be stored in the general flow rate estimation formula storing part 33 and the flow rate estimation formula of the objective blood pump to be stored in the flow rate estimation formula storing part 35 in the flow rate estimation device 30B of the blood pump according to the embodiment 2 may be stored in the predetermined storage medium (for example, a CD-ROM). In this case, by allowing a computer system to read the flow rate estimation formulae stored in the storage medium, it is possible to use the computer system as the flow rate estimation device 30B of the blood pump. Accordingly, with the use of such a storage medium, it is possible to perform the treatment using the implantable blood pump more properly.

Here, in the blood pump system 100B (and the flow rate estimation device 30B of the blood pump) according to the embodiment 2, the general flow rate estimation formula storing part 33 and the flow rate estimation formula forming part 34 may be omitted. This is because that the respective parts are provided for performing functions necessary in performing the first step before shipping, and hence, these parts are not prerequisite in the blood pump system 100B (and the flow rate estimation device 30B of the blood pump) after shipping.

[Embodiment 3]

An embodiment 3 is an embodiment with respect to a flow rate estimation method of a blood pump described in claim 4 of the present invention and a flow rate estimation device of a blood pump and a blood pump system to which the flow rate estimation method of a blood pump is applied.

Figure 12:
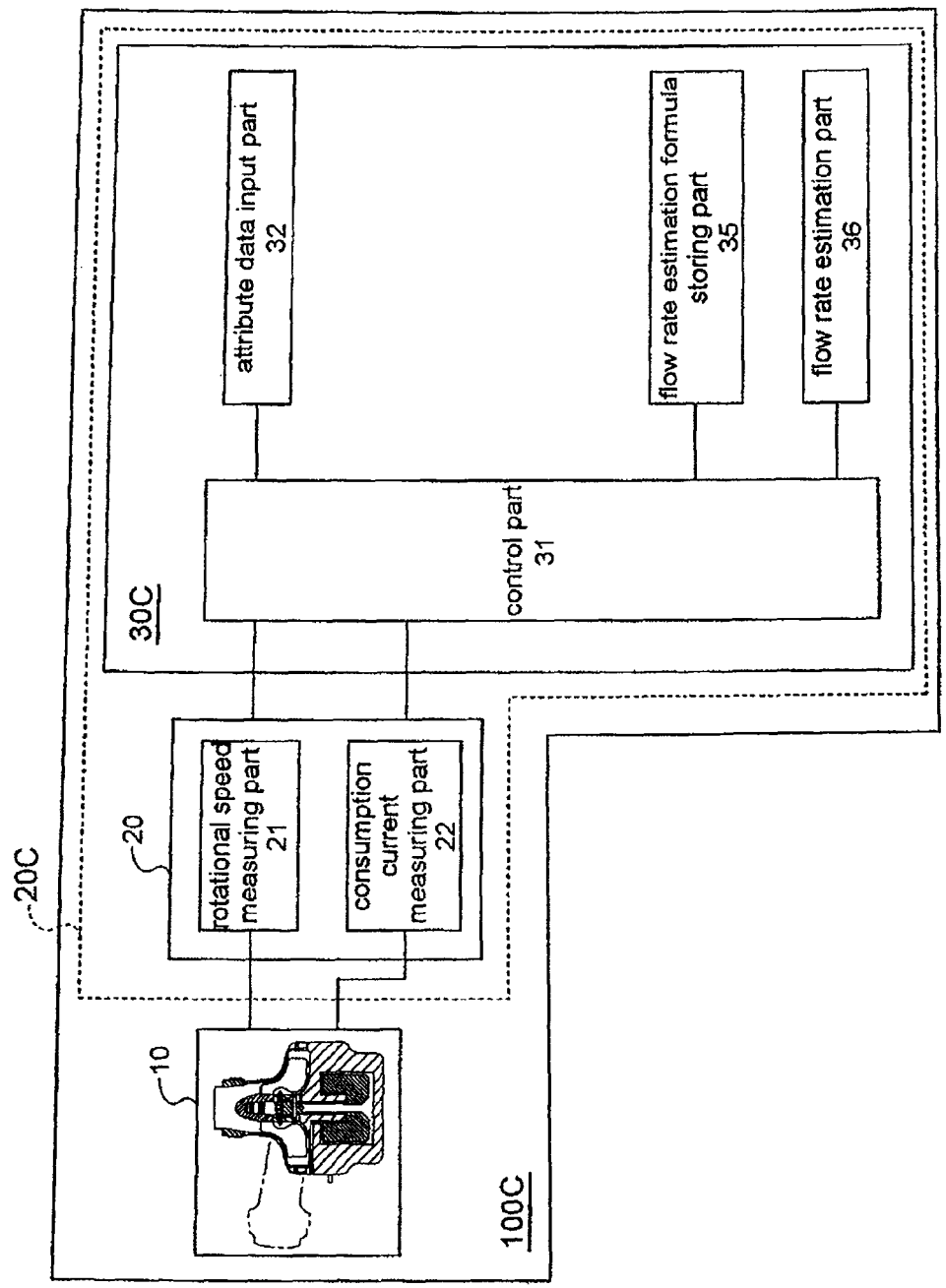
FIG. 12 is a view for explaining a blood pump system according to an embodiment 3.

FIG. 12 is a view for explaining a blood pump system according to the embodiment 3 of the present invention. The blood pump system 100C (and the flow rate estimation device 30C of the blood pump) according to the embodiment 3 have, as shown in FIG. 12, the same constitution as the blood pump system 100B (and the flow rate estimation device 30B of the blood pump) according to the embodiment 2 except for the point that the embodiment 3 is not provided with the general flow rate estimation formula storing part 33 and the flow rate estimation forming part 34.

Figure 13:
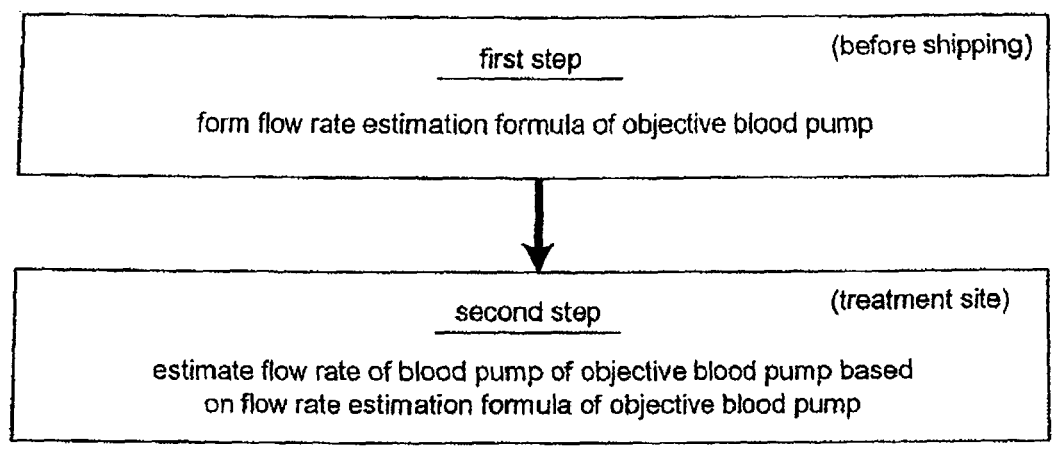
FIG. 13 is a view for explaining a flow rate estimation method of a blood pump according to the embodiment 3.
Figure 14:
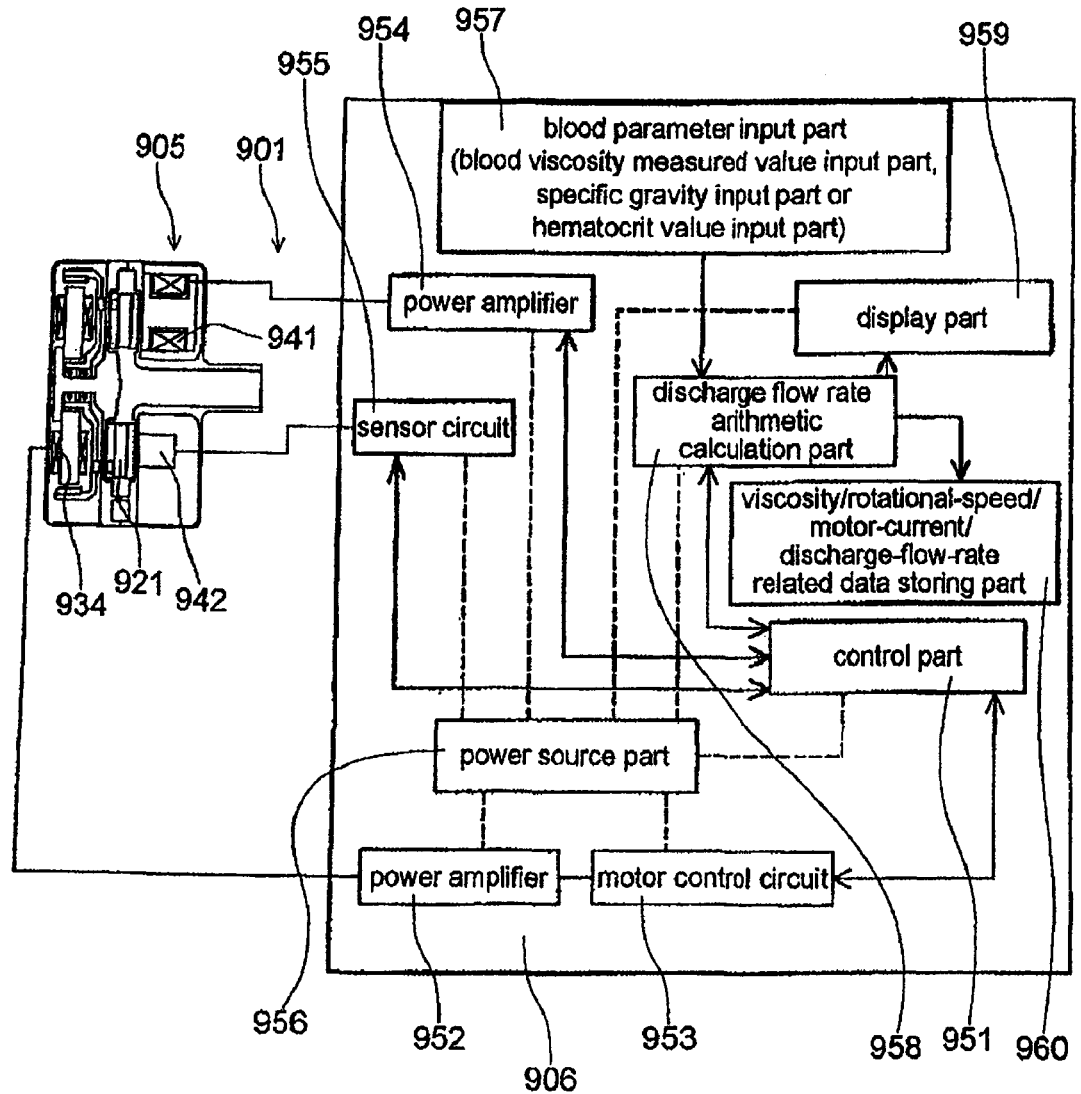
FIG. 14 is a view for explaining a conventional blood pump system.
Figure 15:
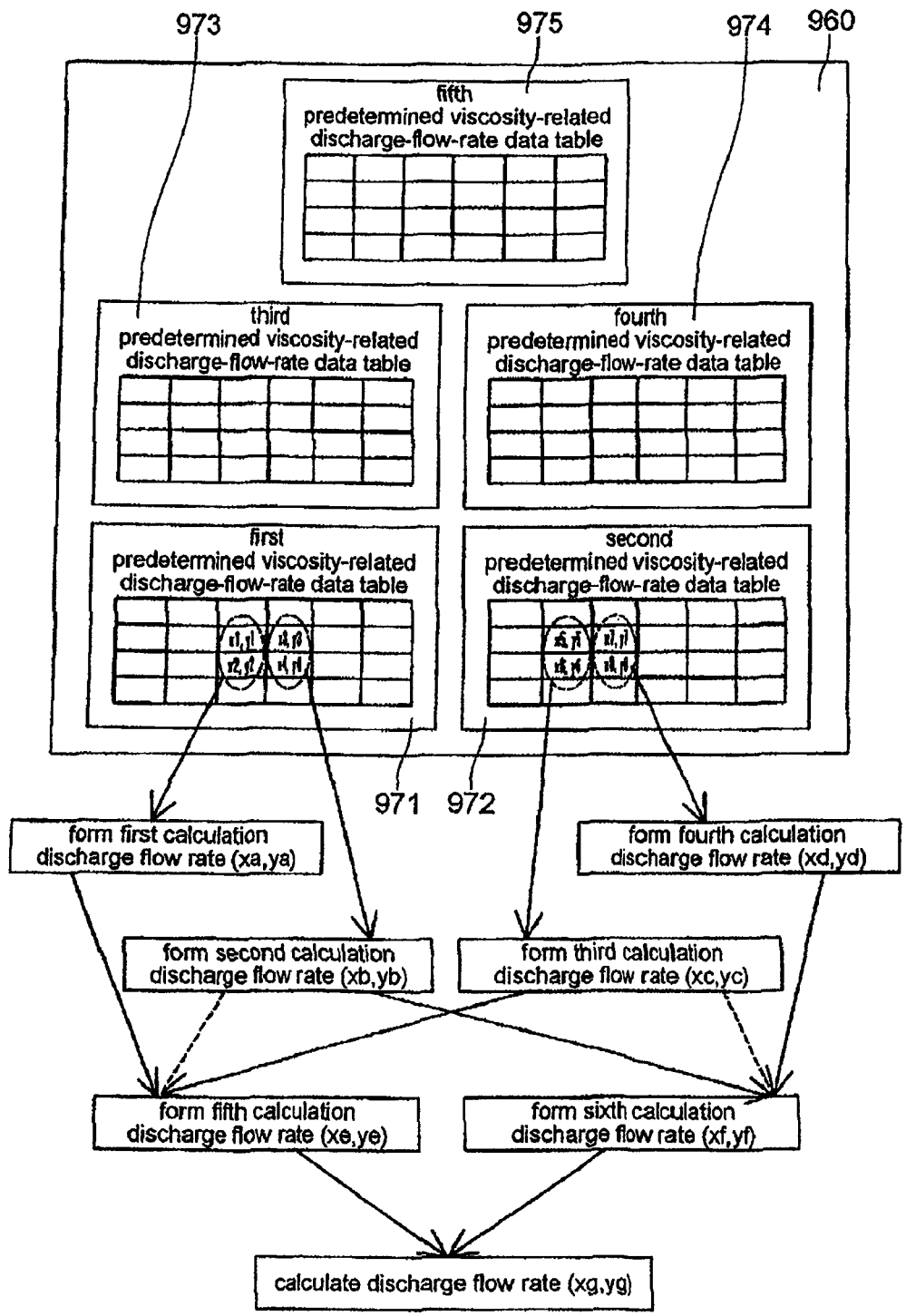
FIG. 15 is a view for explaining a flow rate estimation method of the conventional blood pump.

FIG. 13 is a view for explaining a flow rate estimation method of the blood pump according to the embodiment 3. The flow rate estimation method of the blood pump according to the embodiment 3 is constituted of a first step and a second step as shown in FIG. 13.

(First Step)

The first step is a step in which the flow rate of the blood pump when the rotational speed of the motor and the consumption current of the motor of the objective blood pump 10, and the attribute data of the test liquid are respectively changed is measured using the flow meter (such as a flow meter for industrial use), and the flow rate estimation formula, which constitutes the flow rate estimation information which describes the relationship among the rotational speed of the motor, the consumption current of the motor and the flow rate of the blood pump of the objective blood pump 10, and the attribute data of the test liquid, is formed. As the test liquid, for example, water and a mixed solution of water and glycerin which is adjusted to a plurality of viscosities are used. As the attribute data of the test liquid, the viscosity $\mu$ and the density $\rho$ are used.

The first step is usually performed for every objective blood pump before shipping the objective blood pump 10.

(Second Step)

The second step is a step in which the rotational speed N of the motor and the consumption current I of the motor of the objective blood pump 10 implanted inside the body of the patient, and the attribute data Z of the blood of the patient are measured, and the flow rate Q of the blood pump of the objective blood pump 10 is estimated based on the flow rate estimation formula and these values N, I and Z. As the attribute data of the blood of the patient, the viscosity $\mu$ and the density $\rho$ are used. The second step is substantially equal to the second step of the embodiment 1 and the embodiment 2.

The second step is performed after implanting the objective blood pump 10 inside the body of the patient.

In this manner, according to the flow rate estimation method of the blood pump of the embodiment 3, in the first step, the flow rate estimation formula is determined with respect to the objective blood pump 10 on which the flow rate estimation is performed, while in the second step, the flow rate estimation is performed with respect to the objective blood pump 10 based on this flow rate estimation formula, and hence, it is possible to effectively suppress the deterioration of the accuracy of the flow rate estimation result attributed to the individual difference of the property of the blood pump.

The step which forms the flow rate estimation formula in the first step is the originally cumbersome and time-consuming step. This is because to determine the flow rate estimation formula, it is necessary to measure the flow rate by changing the rotational speed of the motor, the consumption current of the motor and the attribute data of the test liquid respectively.

However, in the flow rate estimation method of the blood pump according to the embodiment 3, the flow rate estimation formula is formed using the test liquid, and hence, it is possible to finish such a cumbersome and time-consuming first step before shipping.

Further, since the cumbersome and time-consuming first step can be performed before implanting the objective blood pump 10 inside the body of the patient, a burden imposed on the patient is not increased.

Still further, by performing the formation of the flow rate estimation formula for every objective blood pump, it may be possible to perform the flow rate estimation with respect to the objective blood pump with higher accuracy immediately after implanting the objective blood pump inside the body of the patient.

As has been explained above, the flow rate estimation method of a blood pump according to the embodiment 3 is an excellent flow rate estimation method of a blood pump, which can effectively suppress the deterioration of the accuracy of the flow rate estimation result attributed to the individual difference of the blood pump as mentioned above. Accordingly, also with the use of such an excellent flow rate estimation method of a blood pump, it becomes possible to perform treatment using the implantable blood pump more properly.

Further, the flow rate estimation device 30C of a blood pump according to the embodiment 3 can perform the flow rate estimation of the blood pump using the excellent flow rate estimation method of a blood pump, which can effectively suppress the deterioration of the accuracy of the flow rate estimation result attributed to the individual difference of the blood pump as described above. Accordingly, also with the use of such an excellent flow rate estimation device 30C of the blood pump, it becomes possible to perform treatment using the implantable blood pump more properly.

Further, the blood pump system 100C according to the embodiment 3 is a blood pump system provided with the excellent flow rate estimation device 30C of the blood pump, which can effectively suppress the deterioration of the accuracy of the flow rate estimation result attributed to the individual difference of the blood pump as described above. Accordingly, with the use of such an excellent blood pump system 100C, it becomes possible to perform treatment using the implantable blood pump more properly.

Still further, the flow rate estimation formula to be stored in the flow rate estimation formula storing part 35 in the flow rate estimation device 30C of the blood pump according to the embodiment 3 may be stored in the predetermined storage medium (for example, a CD-ROM). In this case, by allowing a computer system to read the flow rate estimation formula stored in the storage medium, it becomes possible to use the computer system as the flow rate estimation device 300 of the blood pump. Accordingly, with the use of such a storage medium, it is possible to perform the treatment using the implantable blood pump more properly.

Although the flow rate estimation method of a blood pump and the blood pump system of the present invention have been explained in conjunction with the above-mentioned respective embodiments, the present invention is not limited to such embodiments and various modifications are conceivable as exemplified below.

(a) In the above-mentioned respective embodiments, the flow rate estimation formula (and the general flow rate estimation formula) is/are used as the flow rate estimation information. However, the present invention is not limited to these embodiments and a flow rate estimation table (and a general flow rate estimation table) may be used as flow rate estimation information so as to obtain the substantially equal advantageous effects.

(b) In the above-mentioned respective embodiments, the blood pump which includes the mechanical seal part is used as the blood pump. However, the present invention is not limited to these embodiments and the present invention can obtain the substantially equal advantageous effects even when other blood pumps which may have the individual difference, the dependency on usage environment or a change along with a lapse of time is used.

(c) In the above-mentioned embodiment 3, the blood pump which includes the DC motor is used as the blood pump. However, even when the blood pump which uses as a motor in place of the DC motor is used, it is possible to obtain advantageous effects substantially equal advantageous effects obtained by the embodiment 3.

(d) In the above-mentioned respective embodiments, a centrifugal pump is used as a blood pump. However, the present invention is not limited to the respective embodiments and even when other blood pump (for example, an axial pump) is used, the present invention can obtain the substantially equal advantageous effects.

(e) In the above-mentioned embodiment 1, a blood flow meter based on the thermal, dilution method is used as the blood flow meter. However, in place of this blood flow meter, other blood flow meter (for example, a blood flow meter based on a dye dilution method, an electromagnetic blood flow meter, an ultrasonic blood flow meter, a blood flow meter based on a transesophageal echocardiography, a blood flow meter based on a transthoracic echocardiography or a blood flow meter based on an electric impedance method) may be used so as to obtain the substantially same advantageous effects as the embodiment 1.

(f) As the flow meter for industrial use which is used in the above-mentioned respective embodiments, it is possible to use an ultrasonic flow meter, an electromagnetic flow meter and other various flow meters for industrial use.

EXPLANATION OF SYMBOLS

10: blood pump (objective blood pump), 11: drive part, 12: pump part, 13: impeller, 14: pump casing, 15: inlet port, 16: outlet port, 17: mechanical seal part, 20: external controller, 21: rotational speed measuring part, 22: consumption current measuring part, 30A, 30B, 30C: flow rate estimation device of blood pump, 31: control part, 32: attribute data input part, 33: general flow rate estimation formula storing part, 34: flow rate estimation formula forming part, 35: flow rate estimation formula storing part, 36: flow rate estimation part, 50: blood flow meter, 100A, 100B, 100C: blood pump system, 901: blood pump system, 905: blood pump, 921: impeller, 934: motor, 955: sensor circuit, 957: blood parameter input part, 958: discharge flow rate arithmetic calculation part, 960: viscosity/rotational-speed/motor-current/discharge-flow-rate relevant data storing part

What we claim is:

1. A flow rate estimation device for estimating a flow rate of an objective blood pump which is implanted inside a body of a patient based on (i) a rotational speed of a motor of the objective blood pump, (ii) a consumption current of the motor and (iii) attribute data of blood of the patient, the flow rate estimation device comprising:

an attribute data input part for inputting attribute data of a test liquid or blood of the patient, a general flow rate estimation information storing part for storing general flow rate estimation information which includes a correction term and which is formed based on (a) rotational speeds of motors of a plurality of blood pumps, (b) consumption currents of the motors, (c) attribute data of a test liquid, and (d) flow rates of the plurality of blood pumps, a flow rate estimation information forming part for forming flow rate estimation information on the objective blood pump by substituting into the correction term measured data on (1) the rotational speed of the motor of the objective blood pump, (2) the consumption current of the motor of the objective blood pump, (3) the attribute data of the blood of the patient or the test liquid and (4) the flow rate of the objective blood pump, a flow rate estimation information storing part for storing the flow rate estimation information formed by the flow rate estimation information forming part, and a flow rate estimation part for estimating the flow rate of the objective blood pump based on the flow rate estimation information stored in the flow rate estimation information storing part using (i) the rotational speed of the motor of the objective blood pump, (ii) the consumption current of the motor of the objective blood pump and (iii) the attribute data of the blood of the patient, wherein the flow rate estimation information forming part is configured for forming the flow rate estimation information on the objective blood pump from the general flow rate estimation information by adding correction corresponding to an offset quantity measured by using the objective blood pump.

2. The flow rate estimation device according to claim 1, wherein the flow rate estimation device further includes a connection part for connecting the flow rate estimation device with a blood flow meter for measuring the flow rate of the objective blood pump.

3. The flow rate estimation device according to claim 1, wherein the flow rate estimation information is a flow rate estimation formula.

4. The flow rate estimation device according to claim 1, wherein the flow rate estimation information is a flow rate estimation table.

5. A blood pump system, comprising:
a blood pump for discharging blood using a rotational force of a motor as a driving power source, and
an external controller for controlling an operation of the blood pump,
wherein the blood pump system further includes the flow rate estimation device according to claim 1.

6. The blood pump system according to claim 5, wherein the blood pump has a mechanical seal part for shaft-sealing a rotational shaft of the motor.

7. A flow rate estimation device for estimating a flow rate of an objective blood pump which is implanted inside a body of a patient based on (i) a rotational speed of a motor of the objective blood pump, (ii) a consumption current of the motor and (iii) attribute data of blood of the patient, the flow rate estimation device of the blood pump comprising:

an attribute data input part for inputting attribute data of a test liquid or blood of the patient, a general flow rate estimation information storing part for storing general flow rate estimation information which includes a correction term and which is formed based on (a) rotational speeds of motors of a plurality of blood pumps, (b) consumption currents of the motors, (c) attribute data of a test liquid and (d) flow rates of the plurality of blood pumps, a measured data storing part for storing measured data on (1) the rotational speed of the motor of the objective blood pump, (2) the consumption current of the motor of the objective blood pump, (3) the attribute data of the blood of the patient or the test liquid (4) the flow rate of the objective blood pump, and a flow rate estimation part for
forming flow rate estimation information on the objective blood pump based on the general flow rate estimation information, which includes the correction term, stored in the general flow rate estimation information storing part, and the measured data stored in the measured data storing part, and
estimating the flow rate of the blood pump in the objective blood pump based on the flow rate estimation information on the objective blood pump using (i) the rotational speed of the motor of the objective blood pump, (ii) the consumption current of the motor of the objective blood pump, and (iii) the attribute data of the blood of the patient, wherein the flow rate estimation part is configured for forming the flow rate estimation information on the objective blood pump from the general flow rate estimation information by adding correction corresponding to an offset quantity measured by using the objective blood pump.

8. The flow rate estimation device according to claim 7, wherein the flow rate estimation device further includes a connection part for connecting the flow rate estimation device with a blood flow meter for measuring the flow rate of the objective blood pump.

9. The flow rate estimation device according to claim 7, wherein the flow rate estimation information is a flow rate estimation formula.

10. The flow rate estimation device according to claim 7, wherein the flow rate estimation information is a flow rate estimation table.

11. A blood pump system, comprising:
a blood pump for discharging blood using a rotational force of a motor as a driving power source, and
an external controller for controlling an operation of the blood pump,
wherein the blood pump system further includes the flow rate estimation device according to claim 7.

12. The blood pump system according to claim 11, wherein the blood pump has a mechanical seal part for shaft-sealing a rotational shaft of the motor.

* * * * *